(12) United States Patent
Wagner et al.

(10) Patent No.: US 11,087,464 B2
(45) Date of Patent: Aug. 10, 2021

(54) SYSTEM AND METHOD FOR MOTION-ADJUSTED DEVICE GUIDANCE USING VASCULAR ROADMAPS

(71) Applicant: Wisconsin Alumni Research Foundation, Madison, WI (US)

(72) Inventors: Martin Gerd Wagner, Madison, WI (US); Paul Francis Laeseke, Madison, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 77 days.

(21) Appl. No.: 16/455,331

(22) Filed: Jun. 27, 2019

(65) Prior Publication Data

US 2020/0410666 A1 Dec. 31, 2020

(51) Int. Cl.
*G06T 7/00* (2017.01)
*G06T 7/246* (2017.01)
(Continued)

(52) U.S. Cl.
CPC ............ *G06T 7/0012* (2013.01); *A61B 34/20* (2016.02); *G06T 7/246* (2017.01); *A61B 6/481* (2013.01); *A61B 6/487* (2013.01); *A61B 6/504* (2013.01); *A61B 2034/107* (2016.02); *A61B 2034/2065* (2016.02); *A61B 2090/376* (2016.02); *G06T 2200/24* (2013.01); *G06T 2207/10121* (2013.01); *G06T 2207/20084* (2013.01); *G06T 2207/30101* (2013.01)

(58) Field of Classification Search
CPC .................................................. G06T 7/0012
See application file for complete search history.

(56) References Cited

U.S. PATENT DOCUMENTS 4,878,115 A 10/1989 Elion
6,788,827 B1 9/2004 Makram-Ebeid
(Continued)

FOREIGN PATENT DOCUMENTS

WO 2019075529 A1 4/2019

OTHER PUBLICATIONS

Atasoy, S., et al., "Real-time respiratory motion tracking: roadmap correction for hepatic artery catheterizations," in [Medical imaging ], 691815-691815, International Society for Optics and Photonics (2008).

(Continued)

*Primary Examiner* — Oneal R Mistry
(74) *Attorney, Agent, or Firm* — Quarles & Brady LLP

(57) ABSTRACT

A system and method is provided for creating motion-adjusted or motion-compensated images of a patient to guide an interventional medical procedure. The method includes displaying a static roadmap and a plurality of dynamic images to show the interventional medical device aligned on the static roadmap using a motion transformation. Alignment of the interventional medical device on the static roadmap is based on a user selection of one of motion compensation of the interventional medical device relative to the static roadmap to produce a plurality of images that do not show patient motion or motion adjustment of the static roadmap relative to the interventional medical device to produce a plurality of images that show patient motion.

23 Claims, 21 Drawing Sheets

(51) Int. Cl.
*A61B 34/20* (2016.01)
*A61B 90/00* (2016.01)
*A61B 34/10* (2016.01)
*A61B 6/00* (2006.01)

(56) References Cited

U.S. PATENT DOCUMENTS

| | | | |
|---|---|---|---|
| 8,423,121 | B2 | 4/2013 | Wang |
| 2008/0275356 | A1 | 11/2008 | Stasz |
| 2009/0099472 | A1 | 4/2009 | Remmert |
| 2010/0191102 | A1 | 7/2010 | Steinberg |
| 2011/0293164 | A1* | 12/2011 | Sato .......................... G06T 7/30 382/132 |
| 2017/0151027 | A1* | 6/2017 | Walker .................... A61B 34/37 |
| 2017/0309016 | A1* | 10/2017 | Klaiman .................... G06T 7/30 |
| 2017/0325898 | A1 | 11/2017 | Isaacs |
| 2020/0222018 | A1* | 7/2020 | van Walsum .......... A61B 6/461 |

OTHER PUBLICATIONS

Badrinarayanan, V. et al, "SegNet: A Deep Convolutional Encoder-Decoder Architecture for Image Segmentation," IEEE Trans. Pattern Anal. Mach. Intell., vol. 39, No. 12, pp. 2481-2495, Dec. 2017.
Baek M. Y. et al., "Clinical outcomes of patients with a single hepatocellular carcinoma less than 5 cm treated with transarterial chemoembolization," Korean J. Intern. Med., Oct. 2018.
Barbu, A. et al, "Hierarchical Learning of Curves Application to Guidewire Localization in Fluoroscopy," in 2007 IEEE Conference on Computer Vision and Pattern Recognition, 2007, pp. 1-8.
Bismuth, V. et al, "A comparison of line enhancement techniques: applications to guide-wire detection and respiratory motion tracking," in Medical Imaging 2009: Image Processing, 2009, vol. 7259, p. 72591M.
Bismuth, V. et al, "Curvilinear Structure Enhancement with the Polygonal Path Image—Application to Guide-Wire Segmentation in X-Ray Fluoroscopy," in Medical Image Computing and Computer-Assisted Intervention—MICCAI 2012, vol. 7511, N. Ayache, H. Delingette, P. Golland, and K. Mori, Eds. Berlin, Heidelberg: Springer Berlin Heidelberg, 2012, pp. 9-16.
Bouix, S., et al., "Flux driven automatic centerline extraction," Medical Image Analysis 9(3), 209-221 (2005).
Boyer T. D. et al, "The role of transjugular intrahepatic portosystemic shunt in the management of portal hypertension," Hepatology, vol. 41, No. 2, pp. 386-400, Feb. 2005.
Canny, J., "A computational approach to edge detection," IEEE Transactions on Pattern Analysis and Machine Intelligence PAMI-8(6), 679-698 (1986).
Davis A. G. et al., "Extrahepatic portal vein puncture and intra-abdominal hemorrhage during transjugular intrahepatic portosystemic shunt creation," J Vasc Interv Radiol, vol. 7, No. 6, pp. 863-866, Dec. 1996.
Dice L.R., "Measures of the Amount of Ecologic Association Between Species," Ecology, vol. 26, No. 3, pp. 297-302, Jul. 1945.
Fidelman, N. et al, "The Transjugular Intrahepatic Portosystemic Shunt: An Update," American Journal of Roentgenology, vol. 199, No. 4, pp. 746-755, Oct. 2012.
Haskal Z. J. et al., "Quality improvement guidelines for transjugular intrahepatic portosystemic shunts," Journal of vascular and interventional radiology, vol. 14, No. 9, pp. S265-S270, 2003.
Hilditch C.J., "Comparison of thinning algorithms on a parallel processor," Image and Vision Computing, vol. 1, No. 3, pp. 115-132, 1983.
Honnorat, N. et al, "Robust guidewire segmentation through boosting, clustering and linear programming," in 2010 IEEE International Symposium on Biomedical Imaging: From Nano to Macro, 2010, pp. 924-927.
Katsanos, K. et al, "Comparative effectiveness of different transarterial embolization therapies alone or in combination with local ablative or adjuvant systemic treatments for unresectable hepatocellular carcinoma: A network meta-analysis of randomized controlled trials," PloS One, vol. 12, No. 9, p. e0184597, 2017.
Kim, J. K. et al, "Extrahepatic portal vein tear with intraperitoneal hemorrhage during TIPS," Cardiovasc Intervent Radiol, vol. 24, No. 6, pp. 436-437, Dec. 2001.
King, A. P., et al, "A subject-specific technique for respiratory motion correction in image-guided cardiac catheterisation procedures," Medical Image Analysis 13(3), 419-431 (2009).
Kishore, S. et al, "Update on Embolization Therapies for Hepatocellular Carcinoma," Curr. Oncol. Rep., vol. 19, No. 6, p. 40, Jun. 2017.
Lessard, S. et al, "Automatically Driven Vector for Guidewire Segmentation in 2 D and Biplane Fluoroscopy," World Academy of Science, Engineering and Technology 54 (2009): 446-450.
Lindeberg T., "Edge Detection and Ridge Detection with Automatic Scale Selection," Int. J. Comput. Vis., vol. 30, No. 2, pp. 117-156, 1998.
Manhart, M., et al, "Self-assessing image-based respiratory motion compensation for fluoroscopic coronary roadmapping," in [2011 IEEE International Symposium on Biomedical Imaging: From Nano to Macro ], 1065-1069, IEEE (2011).
Miraglia R. et al., "Efficacy of transcatheter embolization/chemoembolization (TAE/TACE) for the treatment of single hepatocellular carcinoma," World J. Gastroenterol., vol. 13, No. 21, pp. 2952-2955, Jun. 2007.
Mokdad A. A. et al., "Liver cirrhosis mortality in 187 countries between 1980 and 2010: a systematic analysis," BMC Medicine, vol. 12, p. 145, Sep. 2014.
Naimuddin, S. et al, "Scatter-glare correction using a convolution algorithm with variable weighting," Med. Phys., vol. 14, No. 3, pp. 330-334, May 1987.
Nelder, J. A. et al., "A simplex method for function minimization," The Computer Journal 7(4), 308-313 (1965).
Rammohan A. et al., "Embolization of liver tumors: Past, present and future," World J. Radiol., vol. 4, No. 9, pp. 405-412, Sep. 2012.
Russakovsky O. et al., "ImageNet Large Scale Visual Recognition Challenge," Int. J. Comput. Vis., vol. 115, No. 3, pp. 211-252, Dec. 2015.
Schweikard, A. et al, "Respiration tracking in radiosurgery," Med. Phys., vol. 31, No. 10, pp. 2738-2741, Oct. 2004.
Segars, W. P., et al, "4d XCAT phantom for multimodality imaging research," Medical Physics 37(9), 4902-4915 (2010).
Simonyan K. et al, "Very Deep Convolutional Networks for Large-Scale Image Recognition," CoRR, vol. abs/1409.1556, 2014.
Slabaugh, G. et al, "Variational Guidewire Tracking Using Phase Congruency," in Medical Image Computing and Computer-Assisted Intervention—MICCAI 2007,2007, pp. 612-619.
Slagowski, J. M., et al, "Feasibility of CT-based 3d anatomic mapping with a scanning-beam digital x-ray (SBDX) system," in [Proc. SPIE 9412, Medical Imaging 2015: Physics of Medical Imaging ], Hoeschen, C., Kontos, D., and Flohr, T. G., eds., 941209 (2015).
Socher, R. et al, "A learning based hierarchical model for vessel segmentation," in 2008 5th IEEE International Symposium on Biomedical Imaging: From Nano to Macro, 2008, pp. 1055-1058.
Sorensen, T. J., A method of establishing groups of equal amplitude in plant sociology based on similarity of species content and its application to analyses of the vegetation on Danish commons. , I kommission hos E. Munksgaard (1948). OCLC: 4713331.
Spiegel M. et al., "Towards real-time guidewire detection and tracking in the field of neuroradiology," in Medical Imaging 2009: Visualization, Image-Guided Procedures, and Modeling, 2009, vol. 7261, p. 726105.
Timinger, H., et al, "Motion compensated coronary interventional navigation by means of diaphragm tracking and elastic motion models," Physics in Medicine and Bio-logy 50(3), 491-503 (2005).
Tomasi C. et al, "Bilateral filtering for gray and color images," in Sixth International Conference on Computer Vision (IEEE Cat. No. 98CH36271), 1998, pp. 839-846.
Vercauteren, T., et al, "Diffeomorphic demons: efficient non-parametric image registration," NeuroImage 45(1), S61-72 (Mar. 2009).

(56) References Cited

OTHER PUBLICATIONS

Vincent L., "Minimal Path Algorithms for the Robust Detection of Linear Features in Gray Images," in Proceedings of the Fourth International Symposium on Mathematical Morphology and Its Applications to Image and Signal Processing, Norwell, MA, USA, 1998, pp. 331-338.

Wagner, M. et al, "4D interventional device reconstruction from biplane fluoroscopy," Med. Phys., vol. 43, No. 3, pp. 1324-1334, 2016.

Wagner, M. et al, "Noise reduction for curve-linear structures in real time fluoroscopy applications using directional binary masks: Directional denoising using binary masks," Med. Phys., vol. 42, No. 8, pp. 4645-4653, Jul. 2015.

Wagner, M.G. et al, "Feature-based respiratory motion tracking in native fluoroscopic sequences for dynamic roadmaps during minimally invasive procedures in the thorax and abdomen," in Medical Imaging 2017: Image-Guided Procedures, Robotic Interventions, and Modeling, 2017, vol. 10135, p. 101351H.

Zhu S. et al, "A new diamond search algorithm for fast block-matching motion estimation," IEEE Transactions on Image Processing, vol. 9, No. 2, pp. 287-290, Feb. 2000.

Zhu, Y., et al, "Image-based respiratory motion compensation for fluoroscopic coronary roadmapping," Lecture Notes in Computer Science(6363), 287-294, Springer Berlin Heidelberg (2010). DOI: 10.1007/978-3-642-15711-0 36.

International Searching Authority. International Search Report and Written Opinion for application PCT/US2020/039853. dated Sep. 20, 2020.

\* cited by examiner

SYSTEM AND METHOD FOR MOTION-ADJUSTED DEVICE GUIDANCE USING VASCULAR ROADMAPS

STATEMENT REGARDING FEDERALLY SPONSORED RESEARCH

This invention was made with government support under EB024553 awarded by the National Institutes of Health. The government has certain rights in the invention.

CROSS REFERENCE TO RELATED APPLICATIONS

Not applicable.

BACKGROUND

The present disclosure relates to interventional radiological systems and methods. More particularly, the invention relates to systems and methods for guidance of interventional device deployment in the presence of patient motion.

Interventional radiology is a key component in modern healthcare, decreasing risks and allowing faster recovery times for patients. However, these procedures can be costly, and more importantly, require the complete unison between many complex systems in order to be successful. Generally, interventional radiologists who orchestrate these procedures have to overcome many and often different problems. For example, during the procedure, the radiologist must be able to effectively maneuver not only themselves, but also their instruments around relatively tight spaces. This can be especially difficult because typical imaging systems only permit tight clearances to access the patient (e.g., the bore), and unfortunately the instruments required during a procedure tend to be cumbersome in these tight clearances.

Difficulties also stem from deviations from idealities that originate from the patient, which can include artifacts from patient movement (e.g., breathing), different sized and shaped anatomical structures, and the like. Further, other difficulties stem from accurately acquiring the images needed and in the time permitted, to complete a procedure. For example, some anatomical structures, instruments, and the like, may not appear clear or bright enough in an image. Other examples, stem from the imaging system, where the images have to be acquired, processed, and displayed in a specific amount of time. These issues can become especially difficult if they appear simultaneously, such as acquiring an image of an anatomical region that is difficult to view, while the patient is moving. Thus, the field of interventional radiology has relied heavily on the skill and knowledge of the interventional radiologists to overcome these problems and make decisions to complete a procedure effectively.

An example of a typical and widely used interventional radiology procedure is fluoroscopic image guidance for minimally invasive procedures. This procedure, in particular, trans-arterial embolization, currently plays a pivotal role in managing patients with primary and metastatic tumors in the liver. During a liver embolization procedure, a catheter is guided, via fluoroscopy, to specific branches of the visceral or hepatic arteries, where particles or microspheres are delivered directly into the feeding arteries of tumors (e.g., to prevent further growth of the tumor, reduce blood supply to the tumor, provide localized treatment, etc.). Due to the targeting region, accurate and quick placement of catheters is crucial to minimize procedure time and to achieve favorable oncologic outcomes. In order to effectively place instruments (e.g., catheters, guidewires, etc.), images of the region, along with the instrument need to be displayed. However, some anatomical structures, including the vasculature, are nearly impossible to discern from the fluoroscopic image. Thus, typically, a reference of the vascular system is created by injecting contrast agent to the vasculature region, acquiring a fluoroscopic image of the contrast enhanced vasculature, and displaying a static 2D digital subtraction angiography ("DSA") on the contrast enhanced vasculature, prior to placing or manipulating the instruments.

The DSA vascular image can be overlaid or shown side by side with real-time fluoroscopic images, while the instruments are manipulated until the shape of the instrument coincides with the path of the desired vascular branch. Unfortunately, this approach can be difficult, and time consuming, as the instruments often have to be repositioned. More importantly, this approach fails to consider the nature of this particular anatomical region, specifically that the true shape of the vasculature constantly moves and changes shape due to movement of the patient (e.g., respiratory motion, cardiac motion, etc.). Thus, subtraction artifacts are inherently introduced, even when instructing the patient to perform a breath hold during acquisition of the vascular image to be digitally subtracted. Still further, inaccurate image guidance can stem from failure to consider patient movement, as the DSA image only displays a static image of the vasculature at a specific point in time.

Thus, it would be desirable to have improved systems and methods for interventional device guidance.

SUMMARY

The present disclosure provides systems and methods that overcome the aforementioned drawbacks by providing a system and method for creating motion-adjusted or motion-compensated images of a patient to guide an interventional medical procedure. The method includes displaying a static roadmap and a plurality of dynamic images to show the interventional medical device aligned on the static roadmap using motion compensation. Alignment of the interventional medical device on the static roadmap is based on a user selection of one of motion compensation of the interventional medical device relative to the static roadmap to produce a plurality of images that do not show patient motion or motion adjustment of the static roadmap relative to the interventional medical device to produce a plurality of images that show patient motion.

In accordance with another non-limiting example of the disclosure, a method is provided for creating motion-adjusted images of a patient to guide an interventional medical procedure. The method includes acquiring a first plurality of images of a patient having non-contrast enhanced vasculature, acquiring a second plurality of images of the patient having contrast enhanced vasculature, and generating a static roadmap of vasculature of the patient using the first plurality of images and the second plurality of images. The method also includes generating a motion model of the patient using the first plurality of images and the second plurality of images, acquiring a third plurality of images of the patient with an interventional medical device deployed within the patient, and generating motion tracking data of one of the patient or the interventional medical device using the third plurality of images. The method also includes generating a motion transformation using the motion tracking data and the motion model and displaying the static roadmap and the third plurality of images to show the interventional medical device aligned on the static roadmap using the motion transformation. Alignment of the interventional medical device on the static roadmap is based on a user selection of one of motion compensation of the interventional medical device relative to the static roadmap to produce a plurality of images that do not show patient motion or motion adjustment of the static roadmap relative to the interventional medical device to produce a plurality of images that show patient motion In accordance with another non-limiting example of the disclosure, a fluoroscopy imaging system is provided that includes an x-ray source assembly coupled at one end and a x-ray detector array assembly coupled at an opposing end and a computer system. The computer system is configured to control the x-ray source assembly and the x-ray detector array assembly to acquire a first plurality of images of a patient having non-contrast enhanced vasculature and control the x-ray source assembly and the x-ray detector array assembly to acquire a second plurality of images of the patient having contrast enhanced vasculature. The computer system is further programmed to generate a static roadmap of vasculature of the patient using the first plurality of images and the second plurality of images, generate a motion model of the patient using the first plurality of images and the second plurality of images, and control the x-ray source assembly and the x-ray detector array assembly to acquire a third plurality of images of the patient with an interventional medical device deployed within the patient. The computer system is further configured to generate motion tracking data of one of the patient or the interventional medical device using the third plurality of images, generate a motion transformation using the motion tracking data and the motion model, and display the static roadmap and the third plurality of images to show the interventional medical device aligned on the static roadmap using the motion transformation. Alignment of the interventional medical device on the static roadmap is based on a user selection of one of motion compensation of the interventional medical device relative to the static roadmap to produce a plurality of images that do not show patient motion or motion adjustment of the static roadmap relative to the interventional medical device to produce a plurality of images that show patient motion.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
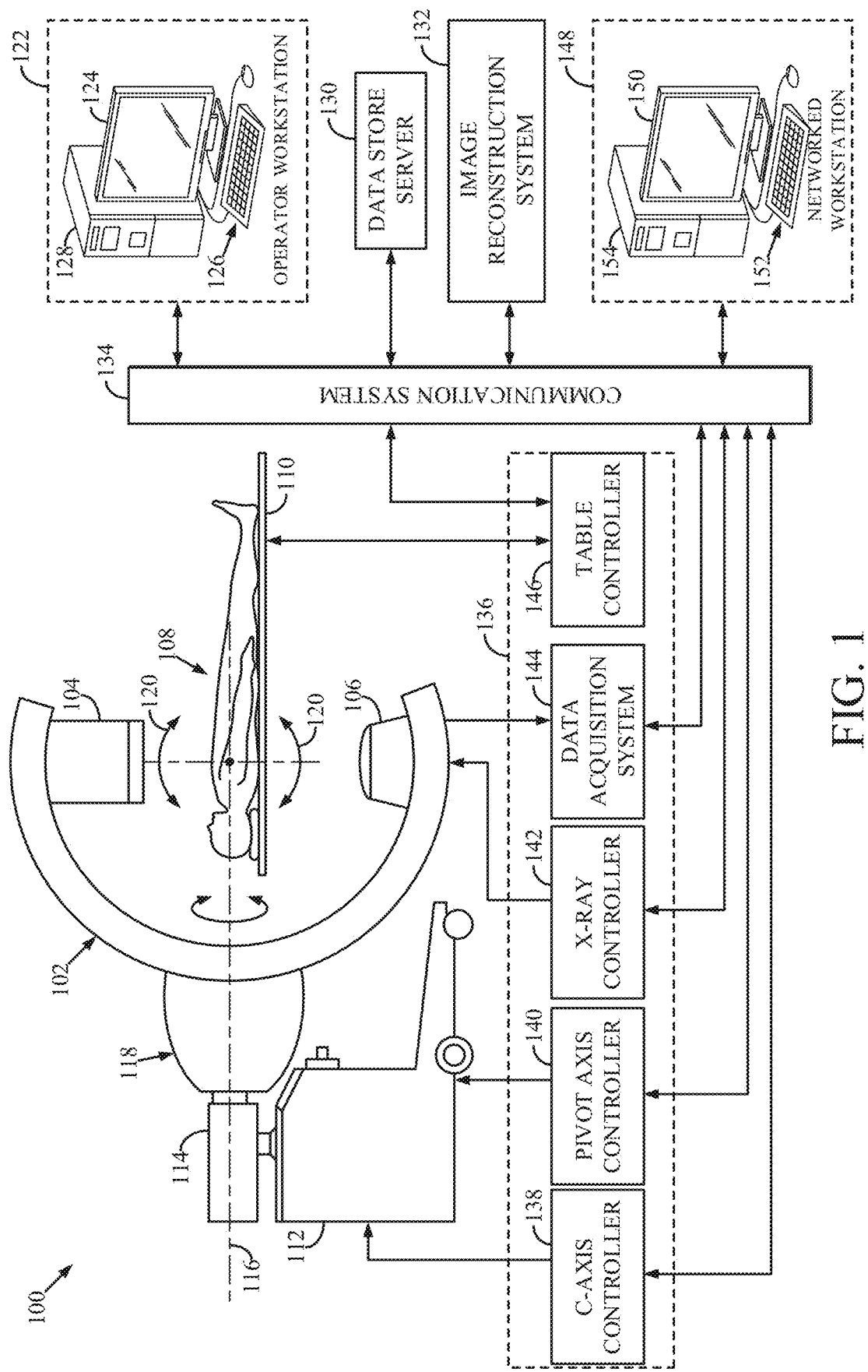
FIG. 1 is a block diagram of an exemplary "C-arm" x-ray imaging system, according to some non-limiting examples of the present disclosure.

Before any non-limiting examples of the invention are explained in detail, it is to be understood that the invention is not limited in its application to the details of construction and the arrangement of components set forth in the following description or illustrated in the following drawings. The invention is capable of other non-limiting examples and of being practiced or of being carried out in various ways. Also, it is to be understood that the use the phraseology and terminology used herein is for the purpose of description and should not be regarded as limiting. Furthermore, the use of "right", "left", "front", "back", "upper", "lower", "above", "below", "top", or "bottom" and variations thereof herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Unless otherwise specified or limited, phrases similar to "at least one of A, B, and C," "one or more of A, B, and C," and the like, are meant to indicate A, or B, or C, or any combination of A, B, and/or C, including combinations with multiple or single instances of A, B, and/or C.

As used herein, the term, "controller" includes any device capable of executing a computer program, or any device that includes logic gates configured to execute the described functionality. For example, this may include a processor, a microcontroller, a field-programmable gate array, a programmable logic controller, etc.

As described above, current fluoroscopy guidance systems fail to address problems with patient movements (e.g., movement due to respiration, cardiac movement, etc.). These problems include artifacts introduced from the DSA procedure, where the vasculature constantly moves and, thus, the DSA image is only a snapshot of the vasculature at a particular moment in time. This can lead to guidance inaccuracies as the target region is static, even though the vasculature and the instrument (e.g., due to the moving vasculature) are constantly in motion. Additionally, the static DSA image, without motion compensation, may require the interventional radiologist to reposition, remove, or reinsert the instrument to complete the procedure. This increase in procedure time increases radiation exposure for the patient, and may require additional doses of contrast agents to effectively see the instrument.

Prior attempts have been made to address and compensate for the motion of the patient. For example, external sensors (e.g., electrocardiogram ("ECG") electrodes, ultrasonic sensors) have been used on individuals to select and display a particular fluoroscopy image, from a series of previously taken images, which is based on sensor data corresponding to a specific point in time of a respiratory cycle. These sensor-based attempts rely heavily on these external sensors, which often fail to effectively correlate with a specific vasculature representation, and which can impede the use of procedural images. Other prior imaging-based systems for motion compensation either require the use of external sensors to be in the field of view, or make inaccurate assumptions for applications (e.g., assuming the surrounding soft tissue corresponds with the vasculature, when in fact, high contrast objects visible in the fluoroscopic images move with different speeds or directions compared to the vasculature).

The present disclosure overcomes these challenges to provide systems and methods that display a static roadmap and the plurality of images to show an interventional medical device aligned on the static roadmap using a motion transformation. Alignment of the interventional medical device on the static roadmap is based on a user selection of one of (i) motion compensation of the interventional medical device relative to the static roadmap to produce a plurality of images that do not show patient motion or (ii) motion adjustment of the static roadmap relative to the interventional medical device to produce a plurality of images that show patient motion.

In one non-limiting example, the systems and methods can track respiratory motion by extracting curvilinear features in fluoroscopic image sequences, rather than relying on additional imaging modalities or external sensors to track the respiratory motion. Additionally, this approach does not require specific structures to be present in the field of view to determine a respiratory state, and is thus suitable for a wider variety of procedures. Further, this approach allows for tracking local deformations of the vasculature, based on respiratory motion, by utilizing a contrast enhanced image sequence under free breathing conditions.

In some non-limiting examples of the present disclosure, the motion-compensating system for fluoroscopy device guidance overcomes the drawbacks associated with prior systems while providing clear advantages. These advantages include decreases in procedure time, increases in procedure accuracy, decreases in the amount of contrast agent required, and decreases in radiation exposure time (e.g., via faster procedures). In some non-limiting examples, the present disclosure includes techniques for respiratory motion tracking and estimation of vasculature deformation in native fluoroscopic images. The motion tracking and estimation can simplify workflows for minimally invasive procedures, such as liver embolization, by allowing for increases in accuracy, and speed (e.g., by decreases in repositioning of instruments) of procedures. Specifically, the systems and method can create a motion model utilizing contrast-enhanced vasculature fluoroscopy images, and extracting curvilinear background features from native (e.g., non-contrast) fluoroscopy image sequences. Importantly, these fluoroscopy images do not require the patient to perform a breath hold, and thus these fluoroscopy images can be acquired during free breathing conditions. The two models, which are used to effectuate motion adjustments, establish the relationship between the respiratory state (e.g., inferred from curvilinear background features), and the vascular morphology during that same respiratory state. As such, after acquiring the vascular morphology, as described above, and during a real-time imaging procedure, the curvilinear feature detection is applied to the real-time fluoroscopy image to determine the vessel mask to display. This creates a dynamic motion-adjusted vessel mask, which can be superimposed on the real-time fluoroscopic images that include the interventional medical device.

Turning now to FIG. 1, an example of one imaging system that may be used with the systems and methods of the present disclosure is illustrated. In this non-limiting example, a so-called "C-arm" x-ray imaging system 100 is illustrated. However, this is just one example and fixed-position, single-source, bi-plane, and other architectures may also be readily used with the systems and methods of the present disclosure.

In the non-limiting example of FIG. 1, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination that is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors, in which the detector array panel may be around centimeters in size. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system ("DAS") 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol ("TCP"), the Internet protocol ("IP"), or other known or suitable protocols.

Although the disclosure below will described in reference to the use of a biplane fluoroscopy imaging system (e.g., the "C-arm" x-ray imaging system 100), in other non-limiting examples other imaging systems can be utilized (e.g., a single-plane fluoroscopy imaging system).

Figure 2:
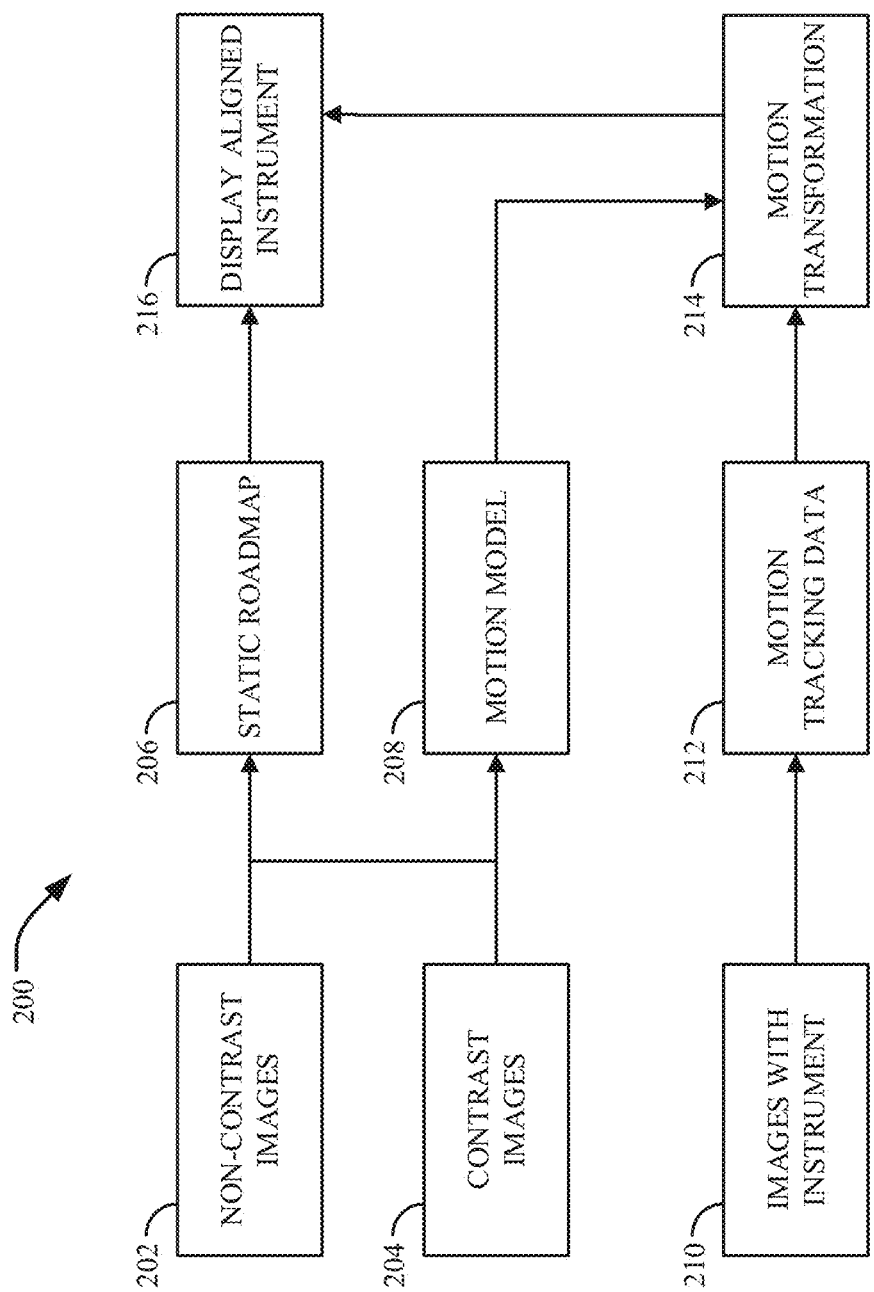
FIG. 2 is an example of a schematic illustration a processing architecture according to some non-limiting examples of the present disclosure.

FIG. 2 is a schematic illustration of a process flow 200 for creating motion-adjusted images of a patient to guide an interventional medical procedure. The process 200 includes acquiring (e.g., via the x-ray imaging system 100) a plurality of images 202 having non-contrast enhanced vasculature, and acquiring a second plurality of images 204 from the patient having contrast enhanced vasculature. Both of these plurality of images can be acquired throughout a full breathing cycle (e.g., beginning during inhalation and completing after exhalation). The process 200 includes generating a static roadmap 206 of the vasculature of the patient and generating a motion model 208 of the patient, where each uses both the first plurality and the second plurality of the images 202, 204. The process 200 further includes acquiring a third plurality of images 210 where an interventional medical device is deployed in the patient (e.g., inserted during the procedure).

The process 200 can also include the generation of motion tracking data 212 for either the patient or the interventional medical device by using the third plurality of images. The process 200 can further include generating a motion transformation 214 using the motion model 208 and the motion tracking data 212. The process 200 then includes the displaying 216 of the static roadmap and the third plurality of images 210 showing the interventional medical device aligned on the static roadmap using the motion transformation 214. The alignment of the interventional medical device is based on a user selection of: (1) motion compensation of the interventional medical device relative to the static roadmap to produce a plurality of images that do not show patient motion (e.g., vasculature motion due to respiratory motion), and (2) motion adjustment of the static roadmap relative to the interventional medical device to produce a plurality of images that show patient motion.

Figure 3:
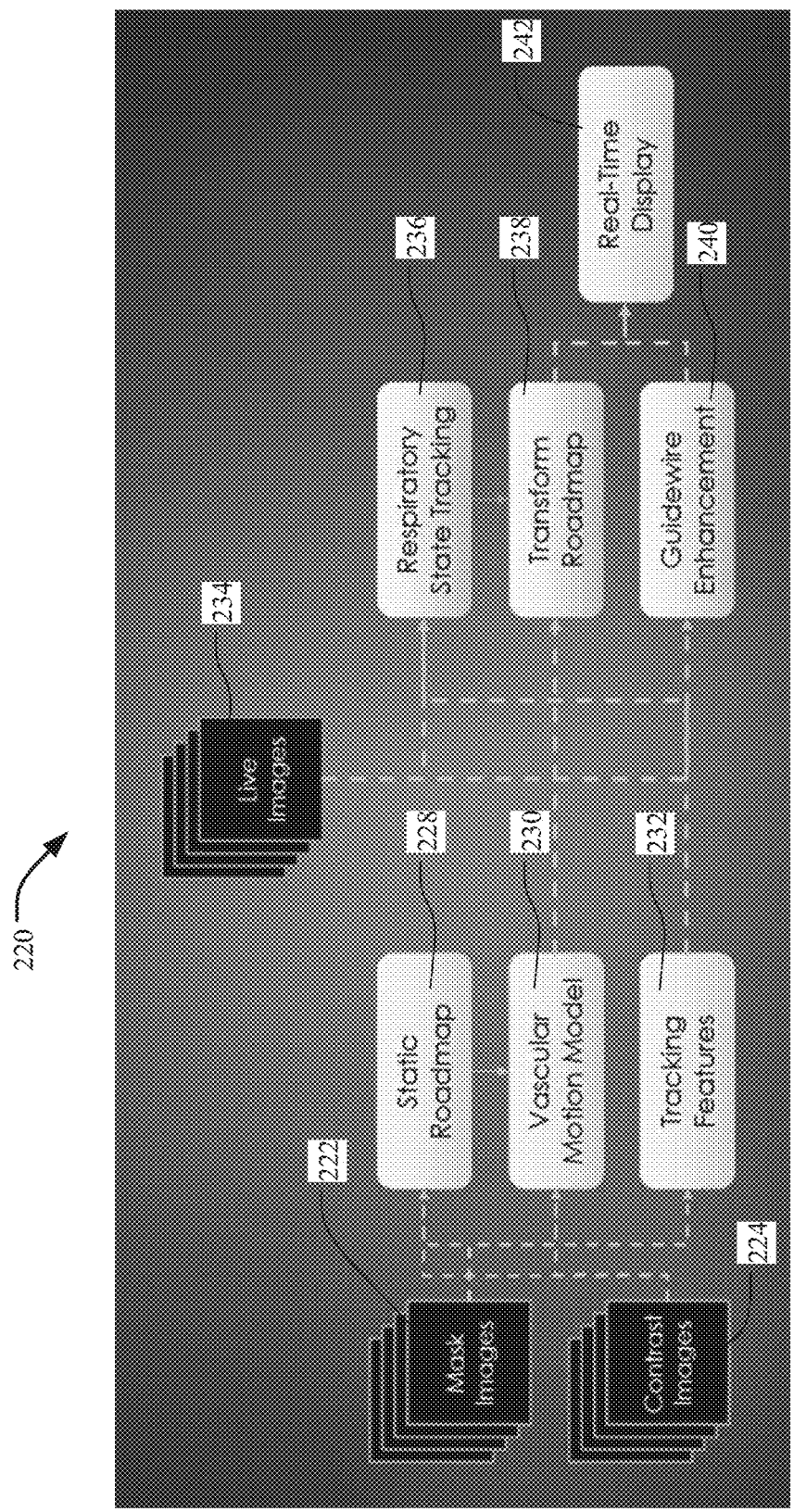
FIG. 3 is a specific process for flow according to one, non-limiting example of a system in accordance with the present disclosure.

FIG. 3 shows a further-detailed process 220, which is a more specific implementation of the process 200 for creating motion-adjusted images of a patient. Specifically, the process 220 includes first acquiring non-contrast images 222 (e.g., mask images) and contrast enhanced images 224 of the patient during a full respiratory cycle (e.g., starting at inhalation and completing at exhalation). In some non-limiting examples, the contrast enhanced images 224 can be acquired using a specific procedure, which ensures that the contrast enhanced images 224 are only acquired during the arterial phase, such that the vasculature of interest is filled with contrast and is well visible in all captured frames. In particular, process 220 includes a step, which automatically detects the arrival of contrast agent in the vasculature to determine the arterial, tissue, and venous phases of the injection. Then, only the arterial phase contrast enhanced images can be utilized. For example, the contrast arrival is estimated by calculating the mean intensity of each frame. Additionally the average intensity over the past frames including the current frame is also calculated. When the current mean intensity is higher than the average intensity for two frames in a row, the algorithm signals that the contrast has arrived. The phases can then be determined by calculating the center of mass in the Y-dimension. Since the contrast is commonly injected in the bottom of the image (e.g., for liver procedures), the center of mass moves down and reaches a turning point towards the end of the arterial phase, which can be used to determine and thus utilize only the arterial phase contrast images (e.g., the images between the events when the contrast arrives and the arterial phase has ended). Subsequently, the center of mass moves up during the perfusion phase and down again during the venous phase.

Once the non-contrast images 222 and the contrast images 224 have been acquired and selected (e.g., utilizing only contrast images during the arterial phase), the process 220 generates subtracted images, which are formed by the subtraction of the contrast images 224 from the non-contrast images 222. These subtracted images can be used to generate a static roadmap 228 of the vasculature of the patient. For example, the static roadmap 228 can be generated by averaging the subtracted images when the respiratory state is consistent, for example, averaging some or all of the subtracted images at the end of expiration (e.g., $\lambda_r=0$). The non-contrast images 222 and the contrast images 224 are also used to generate the vasculature motion model 230, which is a specific implementation of the motion model 208. The process 220 also includes tracking features 232 from the non-contrast images. As discussed in more detail below, tracking features 232 can include the identification and tracking of curvilinear features. Additionally or alternatively, the tracking features 232 can include the identification and tracking of the center of mass within non-contrast images, as discussed below (e.g., with regard to the 3D guidance system).

The process 220 further includes acquiring a plurality of live images 234 that include an interventional medical instrument in the images, and which are used to track the respiratory state 236, which is a specific form of motion tracking data (e.g., with regard to the process 200). The plurality of live images 234 are also used to extract the interventional medical instrument form the plurality of live images 234. Once extracted, the image of the medical instrument can be enhanced (e.g., compressed, elongated, changed in color, etc.) as indicated at step 240.

As will be further described, the process 220 also includes using the tracking of the respiratory state 236 and the vasculature motion model 230 to generate a transformed roadmap 238. In one case, the transformed roadmap 238 can be motion compensation of the image of the medical instrument relative to the static roadmap 238. Alternatively, in another case, the transformed roadmap 238 can be a motion adjustment of the static roadmap relative to the image of the medical instrument (e.g., extracted from the live images 234). The process 220 can generate a real-time display 242 of the live images 234, along with the transformed roadmap 238 in either of at least two configurations. In the first configuration, the live images 234 and the static roadmap 228 are displayed and the transformed roadmap 238 is the motion compensation of the image of the medical device, which is overlaid on the roadmap 238. In the second display, the live images 234 and the image of the medical device are displayed, and the transformed roadmap 238 is the motion compensation applied to the static roadmap 228 to show patient movement. The interventional radiologist can switch between each of the first display and the second display to change which image is motion compensated (e.g., the medical instrument or the static roadmap), based on the interventional radiologist user selection.

Figure 4:
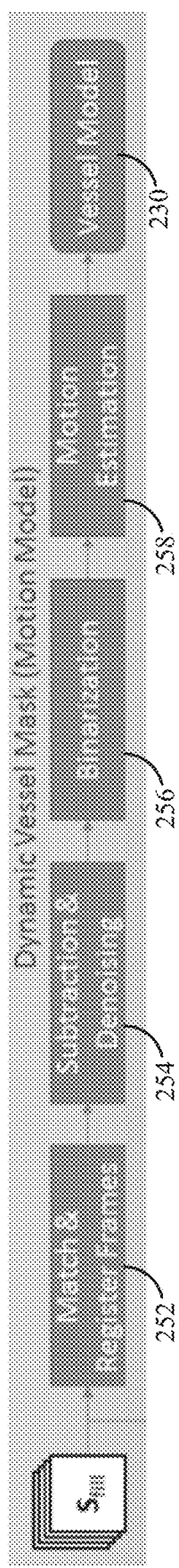
FIG. 4 is a flowchart setting forth one, non-limiting example of a process for creating a vasculature model in accordance with the present disclosure.

FIG. 4 shows an example for specific processes to generate the vasculature motion model 230. The vasculature motion model 230 utilizes subtracted images, which are generated by subtracting the contrast fluoroscopy images

224 from the non-contrast fluoroscopy images 222. However, prior to subtraction, the non-contrast fluoroscopy images 222 and the contrast fluoroscopy images 224 are matched and registered at step 252, which ensures that each image within the non-contrast fluoroscopy images 222 effectively corresponds in time with each image within the contrast fluoroscopy images 224. At step 252, the non-contrast image sequence can be defined as $I_t^N(x)$, and the contrast image sequence can be defined as $I_t^F(x)$. In both image sequence identifiers, t represents the acquisition time for a given image. Then, each contrast image is matched to a non-contrast image, such that the mean squared error between respective images is minimized. For example, the image $I_{\psi(t)}^N(x)$ represents the non-contrast frame that corresponds to the contrast frame acquired at time t, and can be determined by equation 1. For example, equation 1 determines for a given contrast image acquired at time t, the time point $t_m$ of the corresponding non-contrast image. Thus, equation 1 returns a value that is the index of the non-contrast frame that corresponds to the given contrast frame. In some non-limiting examples, if more than one non-contrast image (e.g., 5) correspond to a given contrast image, the non-contrast images can be averaged to generate an average non-contrast image to be subtracted with the corresponding contrast image, as will be discussed below.

$$\psi(t) = \operatorname*{argmin}_{t_m} \sum_{\forall \chi} (I_t^F(\chi) - I_{t_m}^N(\chi))^2 \qquad (1)$$

Although image pairs may correspond to each other in time, it is not guaranteed that the breathing state of both images are exact. For example, slight differences in the location of organs or other anatomic structures might cause subtraction artifacts. To avoid this issue, a block matching registration technique may be used to register the non-contrast images to the corresponding contrast images. Thus, $I_{\psi(t)}^N$ can be divided into distinct blocks $B_i$ and a translation vector $\Delta_i$ can be estimated for each block by minimizing the variance of the gray valve difference according to equation 2. As shown in equation 2, n represents the number of pixel per block and E[x] represents the expected value of x.

$$\Delta_i = \min_{\Delta_i} \frac{1}{n} \sum_{\forall x \in B_i} (I_t^F(x + \Delta_i) - I_{\psi(t)}^N(x))^2 - E[I_t^F(x + \Delta_i) - I_{\psi(t)}^N(x)]^2 \qquad (2)$$

Figure 5:
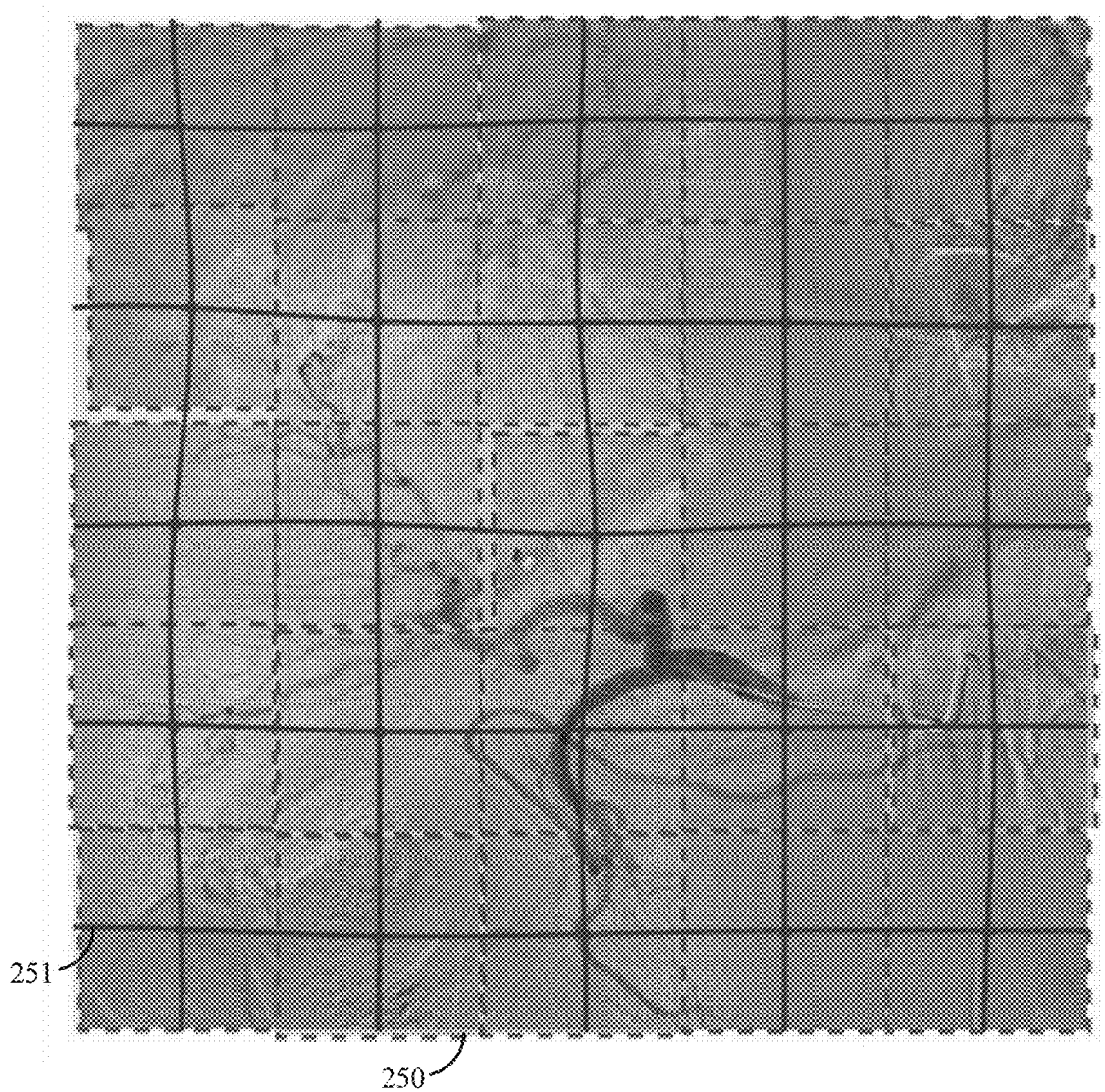
FIG. 5 is an image of the vasculature, with a superimposed spline grid and image blocks used in the generation of the dynamic vasculature model in accordance with the present disclosure.

The final image transformation is then calculated using a cubic spline interpolation. An example of the output from the procedure is shown in FIG. 5. The dotted lines 250 represent the parsed blocks, whereas the solid line 251 represents the calculated cubic spline overlaid on the image. As illustrated in FIG. 5, the light grey regions represent the difference between the fixed image and the registered moving image.

After the corresponding frames have been matched and registered (e.g., step 252), the images are subtracted and denoised at step 254 to generate the subtracted images. For example, the registered image pair is subtracted yielding the difference image $I_t^D(x)$. Since the subtraction increases the noise variance, a Wiener filter is applied to reduce the noise and simplify the segmentation.

Once the corresponding images have been subtracted, and the noise has been mitigated at step 254, a global threshold algorithm can be applied to segment the vasculature, represented by the binarization step 256. This threshold is based on the Euler-number, which is determined by the number of connected components in a binary image minus the number of holes within these objects. For example, given any image, the Euler-number for a threshold smaller than the smallest gray value in the image is one, as all pixels are considered part of the same object.

Figure 6:
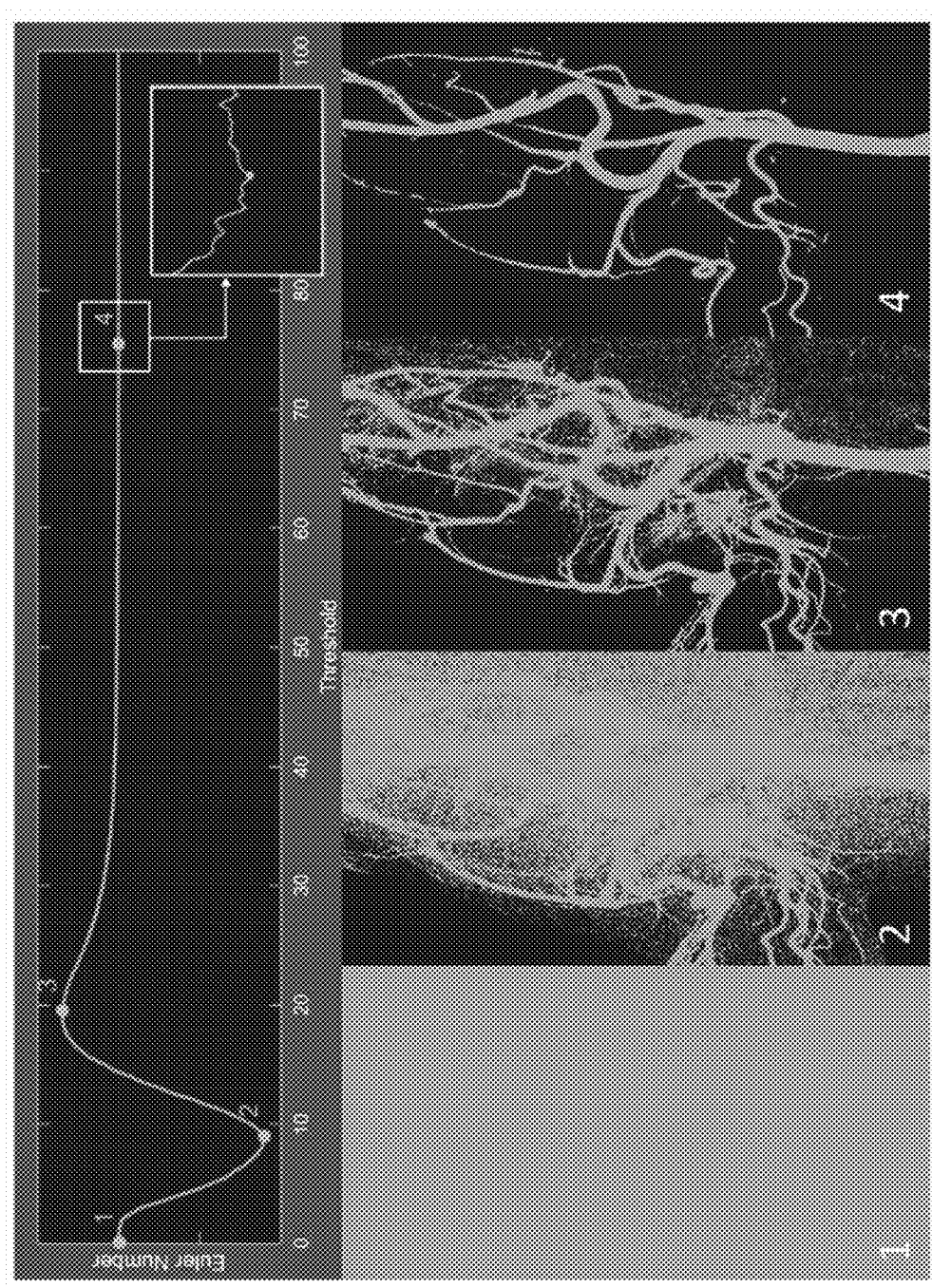
FIG. 6 is a chart of Euler-numbers and corresponding binarization images, used in the generation of the dynamic vasculature model in accordance with the present disclosure.

When the threshold is increased (e.g., just after the denoted "1" in the graph of FIG. 6), holes start to appear within the object, which causes the Euler-number to become negative. Further increase of the threshold causes the segmentation to break up into multiple objects, which increases the Euler-number again (e.g., just after the denoted "2" in the graph FIG. 6). After a second positive peak is reached (e.g., denoted "3" in the graph in FIG. 6), the Euler-number starts to decrease. This local minima (e.g., denoted "4" in the graph in FIG. 6) after the second positive peak (e.g., denoted "3" in the graph in FIG. 6) is used as the threshold within this disclosure. In other words, the threshold values used are those that are higher than those at the second positive peak (e.g., denoted "3" in the graph in FIG. 6). An example of the output of the image after the binarization procedure 256 is shown in FIG. 6, where the four output images are represented, and where each has a specific thresholding value and corresponding Euler number. Typically, the thresholding values used are those that occur after the second maxima (e.g., x>20 thresholding).

Although the procedure to generate vascular motion model 230 involves the binarization step 256, in some non-limiting examples, the binarization step 256 can be omitted or bypassed. This way, for example, the subtracted images are denoised at step 254 and are used directly to estimate motion of the vasculature at step 258, discussed below. In some cases, the avoidance of the binarization step 256 can be desirable for radiologists that are not comfortable viewing binarized images.

The output images from the binarization procedure 256, which represent the segmented vasculature for each frame are denoted as $I_t^B(x)$. After the binarization procedure 256 is completed to yield the segmented images, the motion of the vasculature is estimated at step 258. For example, the deformation of the vasculature due to respiratory motion can be estimated by tracking the pixel motion between adjacent frames using the diffeomorphic demons approach. This approach estimates a translation vector for each pixel, ensuring that the image deformation as well as its inverse are both smooth. The transformation can be described according to equation 3.

$$I_{(t+1)}^B(\chi) = I_t^B(\chi + \delta(\chi)) \qquad (3)$$

Once the transformation is calculated, the respiratory motion of each individual vessel pixel can be parameterized using a single parameter $\lambda_t$, which represents the respiratory state at time t (e.g., at step 230). Thus, the position $p_i$ of each vessel pixel for a given respiratory state can be approximated by the linear function (or other parameterization), according to equation 4.

$$p_i(\lambda_t) = p_i(0) + \lambda_t \cdot (p_i(1) - p_i(0)), \qquad (4)$$

In equation 4, $p_i(0)$ denotes the pixel position at the most exhaled respiratory state (i.e., $\lambda_t = 0$) in the initial contrast enhanced sequence. Conversely, $p_i(1)$ represents the translation vector pointing to its position in the most inhaled state (i.e., $\lambda_t = 1$). In some non-limiting examples, $\lambda_t$ can assume values outside the range [0, 1] during live tracking, if the patient's respiratory motion exceeds the motion of the initial contrast image sequence. However, due to the parameterization (e.g., linear function according to equation 4), the motion of the vasculature can be extrapolated for values outside of the range [0, 1].

In an alternative example of the motion estimation step 258, equation 5 (below), which is a cost function can be used to generate a translation vector for each pixel, that tracks the motion between adjacent mask frames, but which is based on multiple respiratory variables for a given respiratory state, rather than a single respiratory variable for a given respiratory state (e.g., similar to equation 3).

$$c(t_0, t_c, t_d) = -\sum_{\forall i, \forall k} I_k(p_i + t_0 + r_c(k)t_c + r_d(k)t_d)^2 \quad (5)$$

For example, with regard to equation 5, $t_0$ is a constant offset, $t_c$ is the motion vector associated with the chest breathing, and $t_d$ is the motion vector associated with diaphragm breathing. This cost function can also be utilized to generate a single respiratory variable for a given respiratory state by setting $r_c$ equal to 0. The translation vectors $t_c$ and $t_d$ can be separately parameterized using corresponding respiratory parameters (variables) $r_c$ and $r_d$, respectively to generate corresponding parameterizations (e.g., linear functions) for each translation vector and the corresponding respiratory parameter (e.g., similar to equation 4). Thus, as will be discussed below, if the respiratory variable(s) is known, the vasculature motion model 230 can generate the corresponding translation vector(s). In the case of the multiple translation vectors configuration, if the two extracted respiratory parameters (variables) are used to extract the two corresponding translation vectors, then the two corresponding translation vectors can be added to generate a combined translation vector.

In some non-limiting examples, the motion of the vasculature can be estimated at step 258 by using a two-dimensional ("2D") affine image registration with a regular step gradient descent optimization approach, alternatively to the diffeomorphic demons approach. This generates transformation matrices, which describe the deformation of the vasculature and are parameterized using a single parameter $\lambda_t$, which represents the respiratory state at time t (using step 230) or alternatively, the multi-parameter approach that represents multiple respiratory variables for the respiratory state at time t. Specifically, the parameterization is completed for each matrix element, rather than each pixel for the diffeomorphic demons approach. This generates a parameterized matrix, which can be calculated for each respiratory state $\lambda_t$.

Once the motion of the vasculature is estimated at step 258, the vasculature motion model 230 is created, and can be stored, for example, in the operator workstation 122, or the networked workstation 148.

Figure 7:
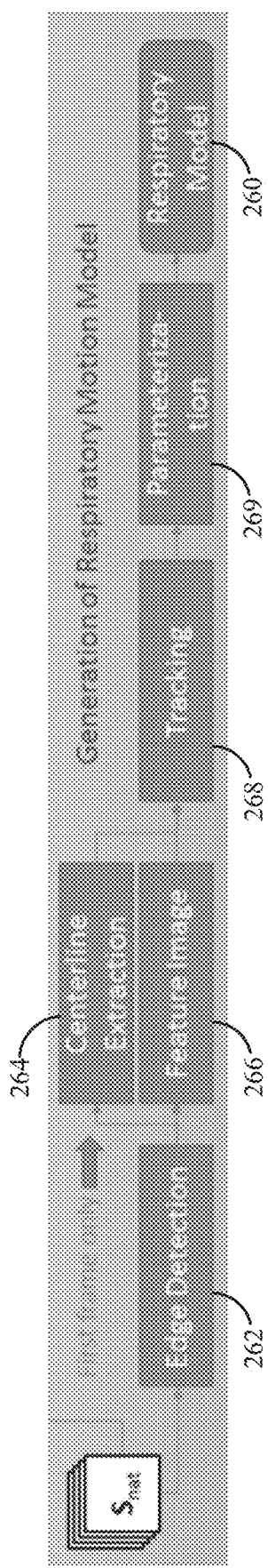
FIG. 7 is a flowchart setting forth one, non-limiting example for generating a respiratory model, within the dynamic vasculature model in accordance with the present disclosure.

FIG. 7 shows an example process for generating a respiratory motion model 260, which is configured to extract a respiratory state(s) from an image, which is to be inputted into the vasculature motion model 230 to generate respiratory motion tracking data (e.g., the translation vector(s)) from the patient (e.g., a specific form of motion tracking data).

As discussed previously, the respiratory motion model 260 generally determines the current respiratory state of the patient (e.g., a specific implementation of 236), by utilizing only native fluoroscopy images, and thus does not need external sensors to determine a breathing state, which has plagued prior systems. The generation of the respiratory motion model 260 begins with generating an average image over all non-contrast images (e.g., the image set defined previously as $I_t^N(x)$). This average image blurs out moving edges, but retains static edges (e.g., edges near the ribs). Then the respiratory motion model 260 proceed to detect edges at step 262 for each of the non-contrast fluoroscopy images (e.g., within the image set defined previously as $I_t^N(x)$), as well as the average image above. In some non-limiting examples, and as implemented, detecting edges 262 can include utilizing a Canny edge detector. For example, the Canny edge detector is applied to the first native image frame (i.e., $I_0^N(x)$) to extract contours along anatomical structures. In other non-limiting examples, rather than utilizing a Canny edge detector, edges can be detected at step 262 by using convolution along with a derivative of a Gaussian kernel.

Figure 8:
FIG. 8 is fluoroscopy image having superimposed and colorized edges, used in the generation of the dynamic vasculature model in accordance with the present disclosure.

Once the edges are detected, the average image that has been outputted from the detecting edges step 262 (e.g., the edge filtered average image) is subtracted from each of the non-contrast images outputted from the detecting edges 262 step (e.g., the edge filtered non-contrast images) to generate edge filtered subtracted images. In some non-limiting examples, the utilization of the average image subtracted form the non-contrast images can eliminate non-moving edges, which can cause issues when tracking features. The edge filtered subtracted images are used to extract centerlines at step 264 by using a topology preserving thinning algorithm, which reduces all contours to a one-pixel thin centerline. Then, a set of curvilinear features can be extracted from the centerlines as a list of connected 2D coordinates by following each contour pixel from endpoint to endpoint. An endpoint is defined as a contour pixel which is connected to only one other contour pixel or a branch point, which is connected to more than two contour pixels. The position of each feature f from the first non-contrast image frame, is tracked over the remaining non-contrast image frames, as indicated by step 266 to generate tracking data at step 268. This can be accomplished, for example, by creating a cost image C ($I_t^N$, x), which is formed by first applying a Canny edge detector followed by a Gaussian smoothing filter (or in some cases, convolution along with a derivative of a Gaussian kernel) to a given non-contrast image, and subtracting this from the previously determined average image that has been outputted from the detecting edges step 262. The cost function can then be optimized by utilizing the Nelder-Mead algorithm. An example of a cost image, along with its highlighted curvilinear features superimposed on the cost image, is shown in FIG. 8.

The translation vector $d_i(t)$, which determines how the features move spatially, can be estimated by maximizing the average gray value along the curvilinear feature using equation 6.

$$d_i(t) = \underset{d}{\operatorname{argmax}} \sum_{\forall \chi \in f_i} C(I_t^N, \chi + d). \quad (6)$$

The feature motion can then be approximated by a linear function based on the respiratory state(s). The coordinates of each point $f_{ij}$ of the feature $f_i$ at time t can be described by equation 7. In other words, the movement of the selected feature(s) can be used to generate a linear function that relates the movement of the feature to the respiratory state.)

$$f = f_{ij}(\lambda_t) = f_{ij}(0) + \lambda_t \cdot d_i(1). \quad (7)$$

In the multiple respiratory parameter implementation for a given respiratory state (e.g., using $r_c$ and $r_d$), separate linear functions can be generated (similar to equation 7) which relate the movement of the chest (e.g., the chest features) to the respiratory parameter $r_c$, and which relate the movement of the diaphragm (e.g., the diaphragm features) to the respiratory parameter $r_d$. Using this information, at step 269, parameterization can be completed to form the respiratory model 260.

For the linear function that relates the features with a single respiratory state (e.g., equation 7), some of the features are not suitable for tracking respiratory motion, and are thus not used in equation 7. Thus, a subset is determined, which contains only the reliably tracked features (e.g., the diaphragm and the chest) that contribute to the respiratory state estimation, as indicated by step 268. This subset of features can be created by first letting $|f_i|$ be the number of points in a given feature $f_i$. Then, all features with $|f_i|<25$ are excluded from the subset. In other words, the initially captured features having less than 25 points are omitted. Similarly, only the features with $\|d_i(1)\| \geq 2.5$ mm are used. This means that only the features that have movement lengths greater than 2.5 mm, over the entire respiratory cycle, are used. Thus, the remaining features having generally small movement lengths are omitted. Having a particular required movement length (e.g., translation length) for a given features helps to avoid static features, or those with only little movement. Finally, in order to remove features that were not successfully tracked in all frames, the criterion $c_a$ is calculated and used. The criteria $c_a$ is calculated from the average gray value along each feature over time in the cost image, according to equation 8.

$$c_a(f_i) = \frac{1}{n_t} \cdot \sum_{\forall t} \frac{1}{|f|} \cdot \sum_{\forall x \in f_{ij}(\lambda_t)} C(I_t^C, x). \tag{8}$$

With regard to equation 8, the variable $n_t$ denotes the number of time frames in the contrast enhanced image sequence. The features with $c_a(f_i) < \tau_a$ are excluded from the set of features. In some non-limiting examples, $\tau_a$ can be any number, although according to the present embodiment, the threshold value of $\tau_a = 0.3$ was used, which was empirically determined. The remaining features, which have passed the three criteria above are utilized to determine the respiratory state (e.g., are used in the calculation of equation 7).

Figure 9:
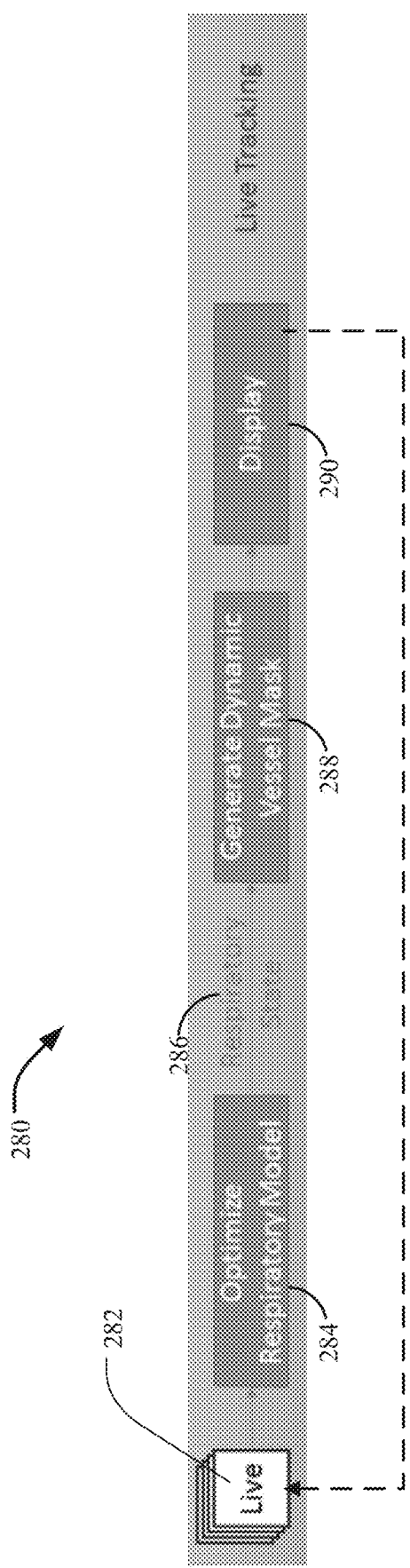
FIG. 9 is a flowchart setting forth one, non-limiting example for generating the real-time tracking system, within the dynamic vasculature model in accordance with the present disclosure.

Once the vasculature motion model 230 and the respiratory motion model 260 have been generated, the real-time system 280 can be utilized (e.g., a specific implementation of steps 234, 236, 238, 240, 242), which is illustrated in FIG. 9. The real-time system 280 starts with the acquiring of live images 282 (e.g., similar to live images 234). Then, a given live image within the live images 282 is optimized within the respiratory motion model 260 to analyze and extract curvilinear features to determine the respiratory state, as indicated by step 284. For example, the respiratory state can be estimated for a given fluoroscopic image frame $I_t^P(x)$ derived from the live fluoroscopy image acquisition. As detailed above, the respiratory state is determined based on the extracted set of curvilinear features. Thus, the cost image $C(I_t^P, x)$ is calculated for the given fluoroscopic image frame $I_t^P(x)$, which is the same as the procedure to calculate $C(I_t^N, x)$. Once calculated, a linear search over the entire range of respiratory states is performed to find the current respiratory state $\lambda_t$, using equation 9 (e.g., which utilizes the respiratory motion model 260).

$$\lambda_t = \arg\max_{\lambda} \sum_{\forall i} \sum_{\forall j} C(I_t^P, f_{ij}(\lambda)). \tag{9}$$

After the current respiratory state $\lambda_t$ has been found, as indicated by step 286, the current state $\lambda_t$ can be the input into the previously generated vasculature motion model 230. This input $\lambda_t$ generates the corresponding translation vector(s) for each vessel pixel. Then, depending on the display choice (e.g., implemented via a user selection), the translation vector(s) for each pixel can be applied to a static roadmap of the vasculature to generate a dynamic vessel mask 288 to motion compensate the vasculature. Alternatively, the translation vector(s) can be inverted and can then be applied to an image of a medical instrument to motion compensate the medical instrument. Either of these implementations can be displayed, as indicated by step 290. Once displayed, the real-time system 280 repeats the steps by first utilizing another live fluoroscopy image (e.g., within the live images 282). Thus, the real-time system 280 performs a real-time display of an accurate representation of the vasculature, which factors in the respiratory state of an individual at any point in time.

The vasculature motion model 230, as discussed above, was evaluated to determine how well the model performed. A quantitative evaluation of the model was performed using a digital 4D CT-phantom (XCAT, Duke University, Durham, N.C., USA), which provides realistic human anatomy including sophisticated respiratory and cardiac motion models. The respiratory motion can be modified by changing the respiratory cycle length, the maximum diaphragm motion and the maximum chest expansion in anteroposterior direction. Each of these parameters can be changed separately. For each time frame, a CT-volume was generated with an isotropic spatial resolution of 0.25 mm. The volume was then projected in the anteroposterior direction using orthographic projection with a field of view of 28.95×21.00 cm. Contrast enhanced images were simulated by setting the attenuation of the vessels in the hepatic artery system to 120 Hounsfield units ("HU"). Additional Poisson noise was added to the images to simulate realistic image quality. In total, four groups of test datasets were generated. Each data set contains 4 sub-datasets and each sub-dataset contains a contrast enhanced and a native image sequence over one respiratory cycle, as well as tracking sequence over four respiratory cycles. A temporal resolution of 5 frames per second was used for all sequences. The respiratory motion parameters were modified during each image sequence to simulate non-regular breathing as shown in table 1, below. Specifically, table 1 shows the four groups of data sets, each having modified respiratory parameters, which include: cycle length, diaphragm motion, chest motion, and contrast to noise ratio ("CNR").

TABLE 1

|  | Group 1 | Group 2 | Group 3 | Group 4 |
| --- | --- | --- | --- | --- |
| Cycle length | 4-7 s | 5 s | 5 s | 4-7 s |
| Diaphragm motion | 2.5 cm | 1.5-3 cm | 2.0 cm | 1.5-3 cm |
| Chest Motion | 1.8 cm | 1.2 cm | 0.6-2.4 cm | 0.6-2.4 cm |
| CNR | 50 | 50 | 50 | 15, 50 |

To evaluate the accuracy of the respiratory motion tracking by itself, the absolute error $e_\lambda$ between the estimated breathing state $\hat{\lambda}_t$ and the true state $\lambda_t$ was calculated according to equation 10.

$$e_\lambda(t) = |\lambda_t - \hat{\lambda}_t| \cdot 100. \qquad (10)$$

Along with the absolute error calculation, the estimated dynamic vessel mask for each frame was also compared to the ground-truth vessel position and shape. The accuracy was measured in terms of the well-known SorensenDice coefficient, as well as the 99th percentile of the perimeter error. Given the ground truth and the estimated vessel segmentation, the perimeter error is calculated for each point along the contour of the estimated vessel segmentation as the distance to the closest contour point in the ground truth segmentation.

Figure 10:
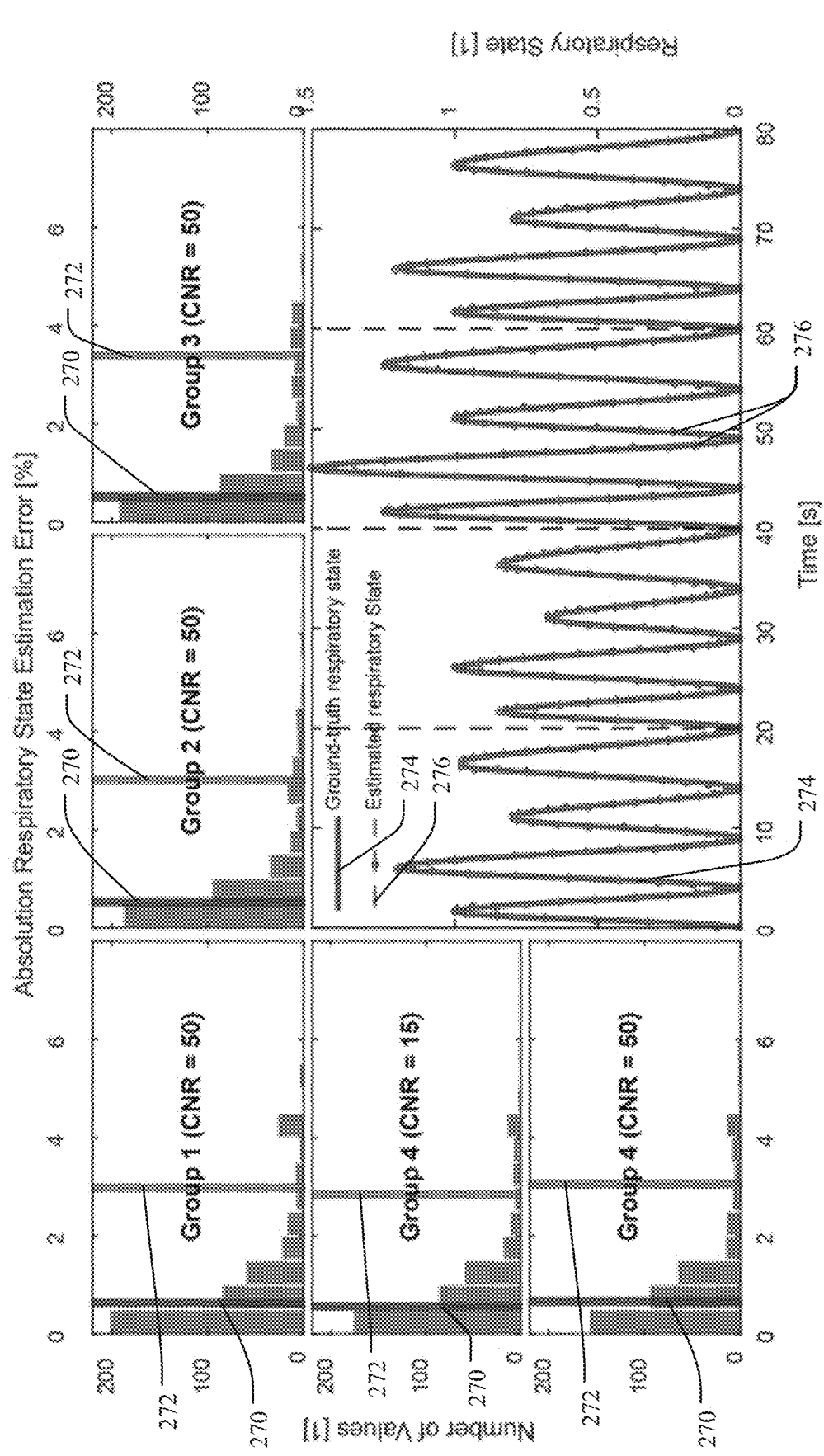
FIG. 10 is a set of correlated graphs illustrating quantitative evaluation of the dynamic vessel model in accordance with the present disclosure.

The quantitative evaluation results from the four groups above, of the respiratory state tracking are shown in FIG. 10. The histograms in FIG. 10 show distribution of absolute errors in percent, where the lines 270 represent the 50th percentile, whereas the bars 272 represent the 90th percentile. The plot on the bottom right of FIG. 10 shows the ground truth (i.e., denoted as the solid line 274) and the estimated respiratory state (i.e., denoted as the dotted line with points 276) of all sequences of group 4. The dashed black vertical lines show the boundary between the different sequences.

For group 1, where only the respiratory cycle length was varied within each image sequence, the absolute error was 1.03+1.22%. For group 2, which varied only the maximum diaphragm motion within each sequence an error of 1.03+1.37% was observed. The error for varying maximum anteroposterior motion in group 3 was 1.03+1.22%. For group 4, where all parameters were dynamically modified, the absolute error was 1.01+1.21% for a CNR of 15, and 1.09±1.25% for a CNR of 50. The accuracy of the estimated dynamic vessel masks yielded similar dice values for all sequences, between 0.94±0.01 and 0.96±0.01. The $99^{th}$ percentile errors of the contour of the estimated vessel masks were 0.92±0.21 mm", 0.86±0.29 mm, and 0.64±0.09 mm, for groups 1 to 3 respectively. The errors for group 4 were 0.96±0.19 mm for a CNR of 15 and 0.86±0.23 mm using a CNR of 50. An overview of all results is shown in table 2, below.

TABLE 2

|  | Respiratory State Error | Sørensen-Dice | 99th percentile |
|---|---|---|---|
| Group 1 (CNR = 50) | 1.03 ± 1.22% | 0.95 ± 0.01 | 0.92 ± 0.21 mm |
| Group 2 (CNR = 50) | 1.03 ± 1.37% | 0.95 ± 0.01 | 0.86 ± 0.29 mm |
| Group 3 (CNR = 50) | 1.00 ± 1.22% | 0.96 ± 0.01 | 0.64 ± 0.09 mm |
| Group 4 (CNR = 15) | 1.01 ± 1.21% | 0.94 ± 0.01 | 0.94 ± 0.19 mm |
| Group 4 (CNR = 50) | 1.09 ± 1.25% | 0.95 ± 0.01 | 0.89 ± 0.23 mm |

Figure 11:
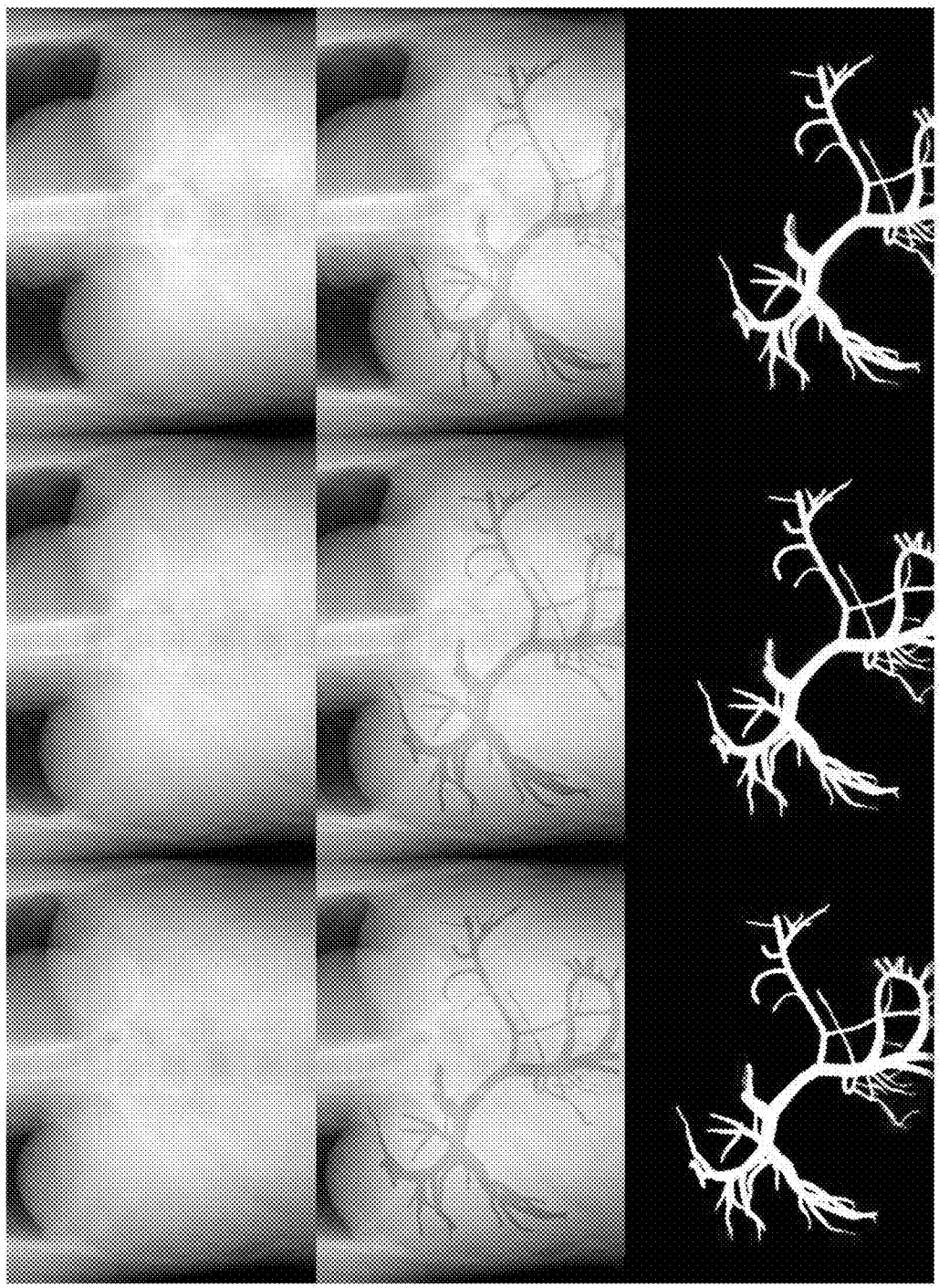
FIG. 11 is a set of correlated images showing a comparison between ground-truth and estimated vasculature images generated from the dynamic vasculature model.

FIG. 11 shows overlays of the ground-truth and estimated vessel masks for different respiratory states. Specifically, the first row of images within FIG. 11, are native image frames used to estimate breathing states for three different time frames. The second row shows the dynamic roadmap (red) overlaid with the native images. The third row shows overlaps of the estimated and ground truth dynamic vessel overlaps. Regions of agreement are shown in white, while the ground truth mask by itself is shown in green. The estimated mask alone is shown in magenta, in the last row.

As discussed above, a vascular roadmap (e.g., the vasculature motion model 230) can be created to provide an accurate representation of the current state of the vasculature, which allows for an accurate reference for an instrument during an interventional radiology procedure. However, during a fluoroscopy procedure the instrument, especially guidewires, may be difficult to discern from the surrounding tissue. Thus, in some non-limiting examples, it is contemplated to provide a clear representation of the instrument by utilizing a neural network to segment an instrument from the fluoroscopy images, and subsequently superimpose the instrument onto the vascular roadmap (e.g., the vasculature motion model 230). In this scenario, a clear representation of the instrument can be displayed on a separate screen, alongside the image of the dynamic vessel mask 288 or the static roadmap 228. Alternatively, rather than being displayed alongside the dynamic vessel mask 288 or the static roadmap 228, the continuous and connected representation of the medical instrument can be overlaid and superimposed with either the static or dynamic image.

Previous systems have attempted to provide a clear representation of the instrument (e.g., a guidewire), but have been unsuccessful. For example one previous approach for guidewire segmentation is to subtract a previously acquired non-contrast image (e.g., mask image) followed by global thresholding. This technique, however, is not suitable for applications with respiratory motion since subtraction artifacts would make it difficult to segment the guidewire reliably. Other techniques for guidewire segmentation in fluoroscopic images involve, for example, the use of line enhancement filters based on Hessian filters, or steerable filters. Unfortunately these attempts do not ensure that the instrument is represented as a single connected path. Attempts to remedy this problem seen by line enhancement filters, include the combined use of path search approaches such as Dijkstra's algorithm, or automatically driven vectors. Similarly, a different approach proposed by Vincent et al. and Bismuth et al. used a local minimal path search based on an intensity-weighted distance transform to detect curvilinear structures. The exponential complexity of a brute force approach can be reduced by evaluating the minimal paths for increasing path lengths. Conversely, optimization based techniques have been proposed using non-rigid registration between adjacent frames or by optimizing a spline using phase congruency to detect curvilinear features.

Finally, machine learning based approaches have been proposed, which use classification approaches to identify small segments which are then combined using linear programming, or hierarchical shape models based on principle component analysis. Many of the proposed approaches require computationally expensive iterative methods, and their robustness of all approaches is dependent on manually defined line detection features.

The deep learning approach proposed in the present disclosure overcomes the problems associated with prior attempts. Due to the curved nature, inconsistent shapes, and unbalanced class frequencies of an instrument including guidewires, previous systems have had difficulty extracting a continuous and connected shape. Rather, prior attempts have extracted disconnected and non-continuous shapes of the instrument. Similarly, with previous attempts including subtraction, patient motion (e.g., respiratory motion) can create unwanted artifacts. The systems and methods according to the present disclosure overcomes the aforementioned drawbacks of previous systems, for example, by segmenting the entire instrument from a given fluoroscopic image, such that a continuous and connected image of the medical instrument is extracted from the fluoroscopy image. Specifically, the extracted continuous and connected image of the medical instrument does not require the use of algorithms or hierarchical shape models. For example, the previous machine learning approaches inputted a fluoroscopic image containing a medical instrument and outputted a disconnected and non-continuous image of the medical instrument. Thus, these previous approaches required other algorithms or hierarchical shape models to join the disconnected segments or portions of the medical instrument to create a continuous representation of the medical instrument. Notably, the systems and methods according to the present disclosure can output a continuous and connected image of the medical instrument for a given fluoroscopy image containing the medical instrument.

Figure 12:
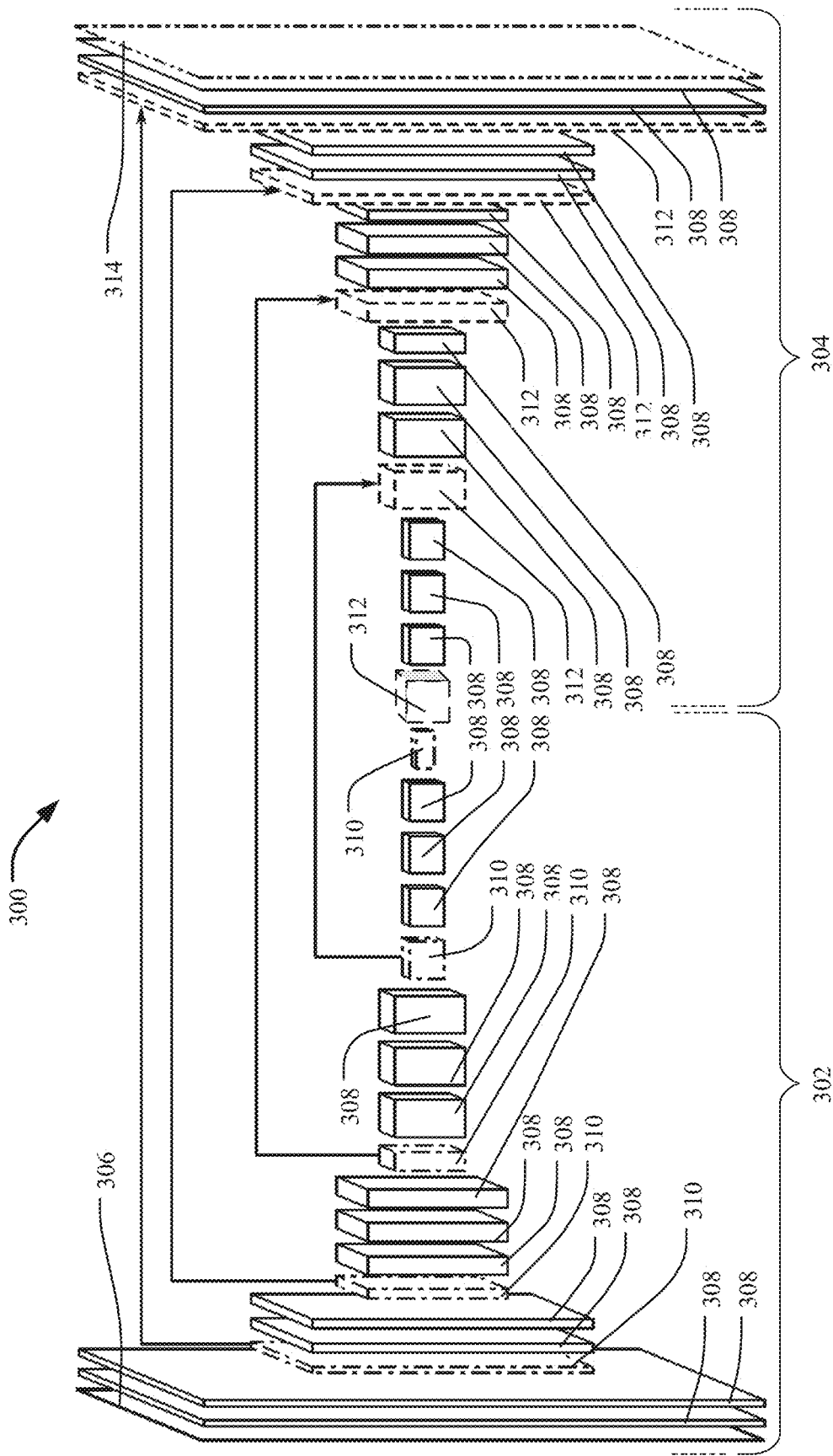
FIG. 12 is a schematic diagram of an architecture for one, non-limiting example of a neural network for the automatic segmentation of medical instruments within a fluoroscopy image in accordance with the present disclosure.

Specifically, the neural network 300, as shown in FIG. 12, was based on the SegNet architecture, using the VGG-16 network with pre-trained weights from the "ImageNet Large Scale Visual Recognition Challenge" dataset. The neural network 300 includes a total of 91 layers, of which are grouped in either an encoder stage 302, or a decoder stage 304. The encoder stage 302 functions generally to reduce information, and is comprised of specific layers. The encoder stage 302 includes a first input layer 306 which is configured to receive a given image. The encoder 302 is followed generally by thirteen layers 308, where each layer 308 includes a convolutional layer, a batch normalization layer, and a rectifier linear unit ("ReLU"). The layers 308 are designated as a solid box in FIG. 12. The encoder 302 also includes five maximum pooling layers 310, which reduce the size of the input image from 1024×1024 pixels to 32×32 pixels. The maximum pooling layers 310 are designated as a dashed-dotted box in FIG. 12. The decoder 304 has generally the same stages as the encoder 302, but are in a reversed order. Additionally, the decoder 304 has replaced the pooling layers 310 with unpooling layers 312, which are designated as a dashed box in FIG. 12. The unpooling layers 312 upsample the reduced information and localize the object. The solid lines that connect a given pooling layer 310 to the corresponding unpooling layer 312, indicate the forwarding of the indices of the maximum values within the pooling window. The decoder 304 further includes a softmax layer 314, which is designated as a dashed dotted-dotted line in FIG. 12, and functions to normalize the output. The last layer of the decoder 304 and of the neural network 300, is a classification layer (not shown) using a weighted cross-entropy loss function for two classes (e.g., guidewire and background).

In order to train the neural network 300, the image data was divided randomly into training (60%), validation (20%) and test (20%) datasets. The training was performed utilizing a single graphics processing unit ("GPU") (e.g., a NVIDIA Geforce GTX 1080 Ti, Santa Clara, Calif., USA). The training was performed using a stochastic gradient descent technique with momentum with an initial learning rate of 0.001, a momentum of 0.9, an L2 regularization of 0.0005, and the batch size set to 1 image. Since the prior probabilities for the two classes are very different (approximately 99.6% of all pixels were background pixels) the class weights were adjusted to avoid biasing the network towards the background class. Therefore, the relative frequencies of each class were determined based on the training data. The class weights were then set to the inverse of the relative frequencies. The neural network 300 was trained for 56,768 iterations (1 epoch), and received a validation accuracy of 99.91%.

In order to improve image quality, the neural network 300 can be trained by providing the current image, and the past two frames, as an input to the neural network 300. Advantageously, this allows the neural network 300 to learn to track moving parts in the image, which are often easier to detect then a static object due to noise. In other non-limiting examples, the neural network 300 can be trained by providing the current image, along with the past four frames.

After training based on the dataset above, the neural network 300 was evaluated by comparing the segmentation results over the test dataset to a mask-subtraction-based segmentation algorithm. A corresponding mask image was created for each test image containing only the anatomic background, assuming no motion occurred between the acquisitions of mask and test image. The same amount of Poisson noise used for the guidewire image was added to the mask image, simulating an actual clinical acquisition. The mask image was then subtracted from the test image, filtered using a directional line enhancement filter, and globally thresholded to extract the guidewire pixels. The intensity threshold was chosen based on the training dataset. The accuracy of the segmentations for both algorithms was measured in terms of the false-positive and false-negative rates, the Hausdorff distance as well as the Sorenson-Dice coefficient. These results are shown below in table 3, which compares the Sorenson-Dice coefficient ("SDC"), false positive rate ("FPR"), false negative rate ("FNR"), and Hausdorff distance ("HSDF") for deep learning and mask-subtraction-based segmentation.

TABLE 3

|  | SDC | FPR | FNR | HSDF |
|---|---|---|---|---|
| Deep Learning | 58.1% | 0.1% | 9.6% | 16.3 px |
| Mask Subtraction | 23.7% | 2.0% | 40.8% | 90.6 px |

Figure 13:
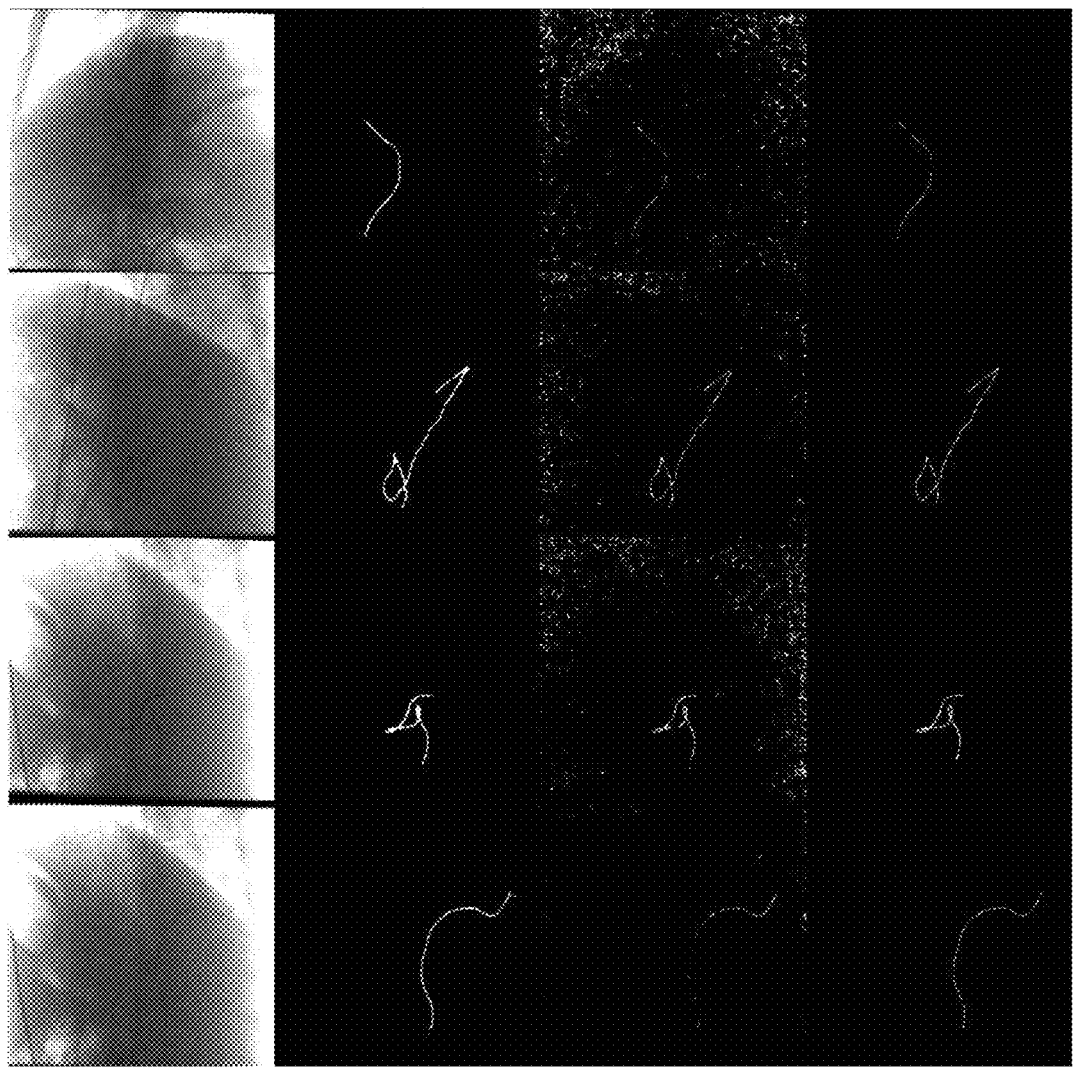
FIG. 13 is a set of images providing a visual representation comparing results between a typical DSA procedure, the output of the neural network of FIG. 12, and a ground-truth image, over four examples.

FIG. 13 visually represents the results from the comparison between the different methods. For example, the first column of images show the starting images, the second column of images are the resulting images outputted from the neural network 300, the third column of images represent the results from the mask subtraction segmentation algorithm, and the last column is the ground truth column (e.g., images of an example of the instrument superimposed on the fluoroscopy images).

In some non-limiting examples, the deep learning approach to segment an instrument (e.g., a guidewire) can be advantageous over prior attempts, in situations where the acquired fluoroscopy images have large intensity variations, include image noise, and have a small device signal relative to the entire image (e.g., in thorax/abdomen procedures). For example, although, the previous subtraction-based method removed large background intensity variations and enabled the use of threshold-based segmentation, accurate segmentation in the presence of noise was still challenging. In fact, the subtraction-based segmentations were often discontinuous or incomplete despite the use of an optimized threshold derived from the training dataset. Additionally, the subtraction-based results were obtained without simulating the respiratory motion that would normally take place between the mask and guidewire images. Thus, the already present subtraction artifacts would be made worse if acquired during respiratory motion, as this can introduce additional, and typically worse subtraction artifacts. As such, the deep learning approach allows an instrument that has a curvilinear shape (e.g., a guidewire) to be accurately segmented.

In some non-limiting examples, components within the vasculature motion model 230 (and the corresponding systems or processes) and the instrument deep learning segmentation approach can be combined. For example, components within the respective systems can be formed to create guidance systems 320, 340.

Figure 14:
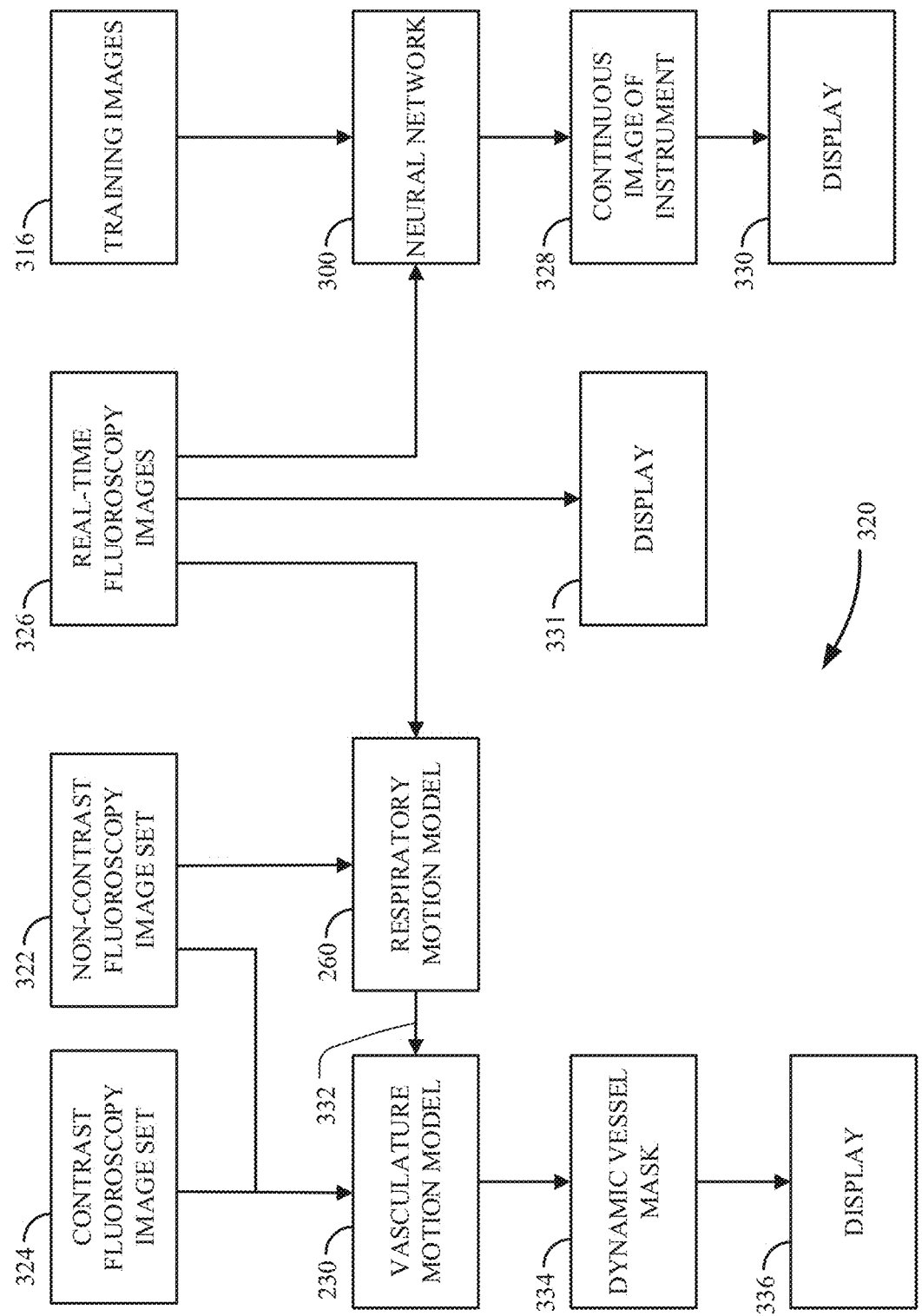
FIG. 14 is a block diagram illustrating an example for implementing a two-dimensional ("2D") fluoroscopy guidance system in accordance with the present disclosure.

FIG. 14 shows a block diagram of the guidance system 320. As shown, the guidance system 320 has similar components that have already been introduced. Thus, the previous description of these components also pertain to the components within the guidance system 320. The guidance system 320 includes the acquisition of a non-contrast fluoroscopy image set 322 and a contrast fluoroscopy image set 324. Each of these image sets, are similar to the previously discussed image sets, and are used to generate both the vasculature motion model 230 and the respiratory motion model 260, as discussed above. Each of the image sets 316, 318 can be acquired prior to the interventional procedure, and the vasculature motion model 230 and the respiratory motion model 260 can be generated prior to the interventional procedure.

While, the vasculature motion model 230 and the respiratory motion model 260 are being generated, or in some cases, prior to the acquisition of the image sets 316, 318 the neural network 300 can be trained. The neural network 300 can be trained using training images 316, which can be, for example, previously acquired fluoroscopy images that include the instrument intended to be used during the procedure. Although this discussion below will be described in reference to a guidewire, other instruments can be used. For example, other curvilineal instruments such as catheters, could be used. However, the neural network 300 would need to be trained for the particular instrument to be used. Alternatively, in some cases, if the neural network 300 has been previously trained to extract a continuous and connected guidewire, in the subsequent procedure, the neutral network 300 need not be trained again prior to the procedure.

Once the neural network 300 is prepared, real-time fluoroscopy images 326 are acquired (e.g., via the x-ray imaging system 100) as the guidewire is inserted into the patient (i.e., the procedure has begun). In some cases, and as illustrated, the real-time fluoroscopy images 322 can be displayed on a display 331 (e.g., similar to the display 150, the display 124, etc.), if the interventional radiologist desires. Correspondingly, a given image within the real-time fluoroscopy images 326 is directed to both the neural network 300 and the respiratory motion model 260. As discussed previously, the given image within the real-time fluoroscopy images 326 that is inputted into the neural network 300, will output a continuous and connected image of the guidewire 328, which can be displayed on a display 330 (e.g., similar to the display 150, the display 124, etc.). Additionally, the given image within the real-time fluoroscopy images 326 is directed to the respiratory motion model 260, which analyzes and subsequently extracts curvilinear features from the given image to be used within the respiratory motion model 260 to determine the respiratory state 332 (e.g., $\lambda_r$). The respiratory state 332 is inputted into the vasculature motion model 230 to determine the corresponding translation vector (s) for each pixel for the respiratory state 332. The translation vector(s) for each pixel is applied to a previously generated static roadmap within the vasculature motion model 230 to generate a dynamic vessel mask 334. The dynamic vessel mask 334 can be displayed on a display 336 (e.g., similar to the display 150, the display 124, etc.).

The displays 331, 330, 336, within the guidance system 320 allow an interventional radiologist to view key features separately. For example, during the procedure, the display 336 shows a motion compensated representation of the vasculature, which factors in the compression, and changes in spatial position of the vasculature during a respiratory cycle. This is advantageous as the vasculature is difficult to view in native, unprocessed fluoroscopy images, and previous segmentation of the vasculature techniques do not show an accurate moving representation of the vasculature, and rather show a static representation of the vasculature. During the procedure, the interventional radiologist can also view a clear representation of a guidewire (or other instrument) on the display 330. In some non-limiting examples, the continuous and connected image of the medical instrument 328 can be adjusted (e.g., increased in size, changed in color, etc.), prior to the display on the display 330. This is advantageous because similarly to the vasculature, some instruments including guidewires are difficult, if not impossible, to view in a native, unprocessed fluoroscopy images. Lastly, the interventional radiologist can view the real-time fluoroscopy images 326 on the display 326. Thus, the interventional radiologist can view whichever screen is desired to effectively guide the guidewire to the target.

In some cases, it may be desired to combine images prior to display, such that the interventional radiologist can view a single display, rather than constantly shifting their focus between the displays (e.g., displays 331, 330, 336). Thus, in some non-limiting examples, a guidance system 340 is provided that allows for a single display, such that the interventional radiologist only needs to view the single display to effectively complete the interventional procedure.

Figure 15:
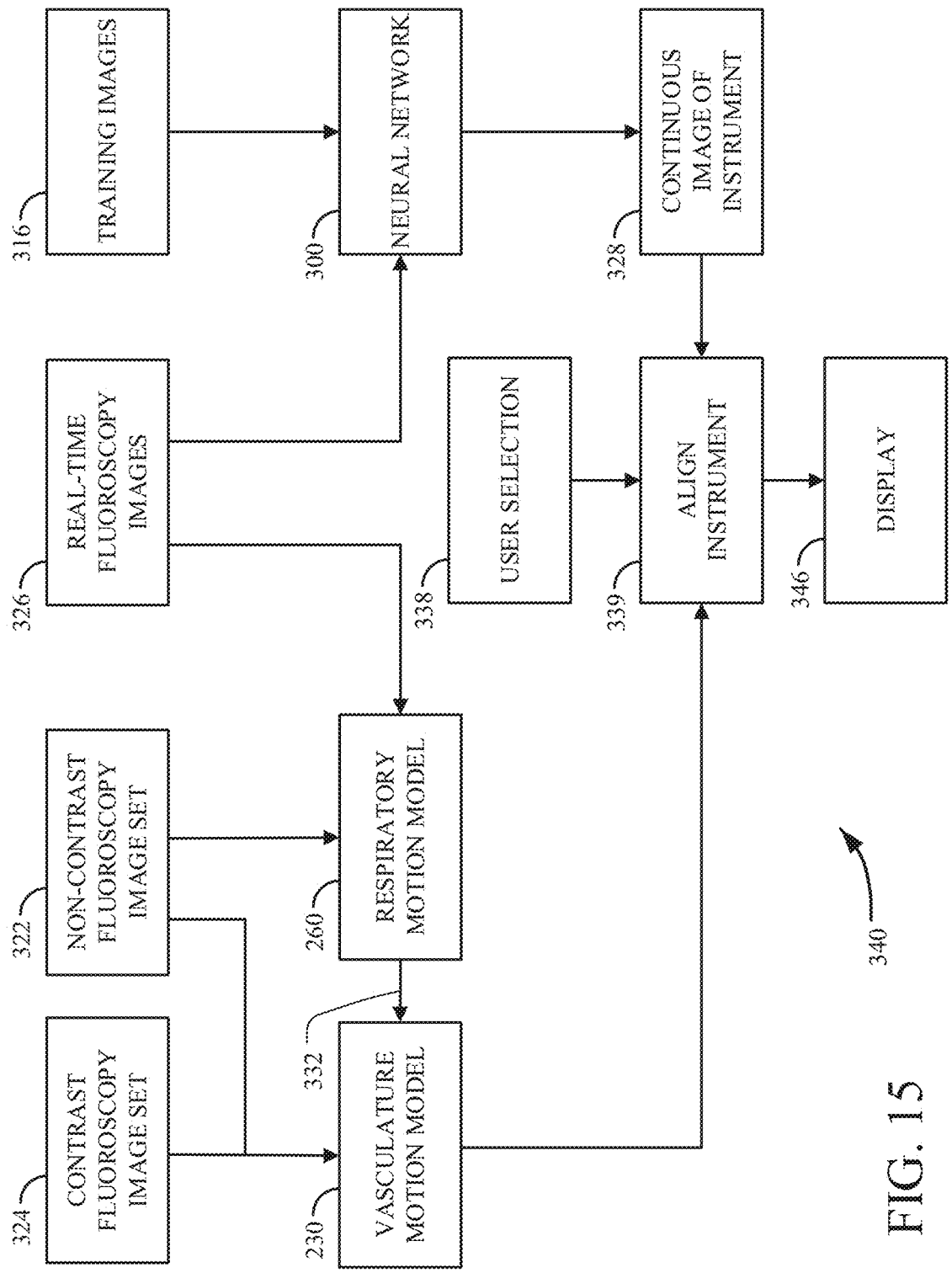
FIG. 15 is another block diagram illustrating an example for implementing another 2D fluoroscopy guidance system in accordance with the present disclosure.

FIG. 15 shows a block diagram of the guidance system 340. The guidance system 340 has similar components which have already been introduced, especially in view of the guidance system 320. Thus, the previous description of these components also pertain to the components within the guidance system 340. For example, the given image within the real-time fluoroscopy images 326 is directed to the respiratory motion model 260, which analyzes and subsequently extracts curvilinear features from the given image to be compared within the respiratory motion model 260 to determine the respiratory state 332 (e.g., $\lambda_r$). Also, the given image within the real-time fluoroscopy images 326 that is inputted into the neural network 300, will output a continuous and connected image of the guidewire 328. However, the continuous and connected image of the instrument 328 is combined in a specific way with the static vasculature roadmap and the translation vector(s) for each pixel for the respiratory state 332 within the align instrument step 339. The way these are combined, for example, how the motion compensation will be applied, depends on a user selection 338 (e.g., an actuated button, a user interface, etc.).

For example, the user selection 338 can select a first state, which applies the inverse of the translation vector(s) for each pixel for the respiratory state 332 to the continuous and connected image of the instrument 328. This motion compensated image of the medical instrument is overlaid with the static vasculature roadmap (e.g., also outputted from the vasculature motion model 230). This output from the first state is displayed on the display 346 (e.g., similar to the display 150, the display 124, etc.). This first state applies the motion compensation to the guidewire, while keeping the vasculature image static (e.g., the static vasculature roadmap). Thus, this first state can be advantageous for the interventional radiologists as the target (e.g., a portion of the vasculature) is stationary. However, the guidewire is compensated for respiratory movement, being moved (e.g., translated, compressed) depending on the particular respiratory state. Thus, the position of the guidewire can be corrected, such that the guidewire is aligned on the static vasculature roadmap. This allows for the interventional radiologist to guide the guidewire to the target location, which is stationary (e.g., the static roadmap) and manipulate the guidewire, such that apparent movement of the guidewire (e.g., on the display) can be only caused by the interventional radiologist.

The user selection 338 can also select a second state of the align instrument step 339. As discussed above, the align instrument step 339 receives the continuous and connected image of the instrument 328, the static vasculature roadmap, and the translation vector(s) for each pixel for the respiratory state 332. However, in the second state, the translation vector(s) for each pixel are applied to the static vasculature roadmap to generate a dynamic vessel mask (e.g., the dynamic vessel mask 334) and the continuous and connected image of the instrument 328 is overlaid with the dynamic vessel mask. This second state applies motion compensation to the image of the vasculature to generate, with subsequent images a "video" of the moving vasculature. This allows the interventional radiologist to clearly view the guidewire relative to an accurate representation of the target vasculature. For example, the desired target point for the guidewire, which is a portion of the vasculature, moves and deforms throughout the respiratory cycle, and ideally coincides with the guidewire (e.g., the guidewire aligns with the dynamic vessel mask 334). Thus, specifically, the vasculature, forms a real-time video, such that the interventional radiologist can accurately guide the guidewire to the target location.

In some non-limiting examples, the guidance systems 320, 340, can be implemented on the x-ray imaging system 100. In some cases, the x-ray imaging system 100 can be modified to effectively run the neural network 300 (e.g., including GPUs, parallel processors, etc.).

Figure 16:
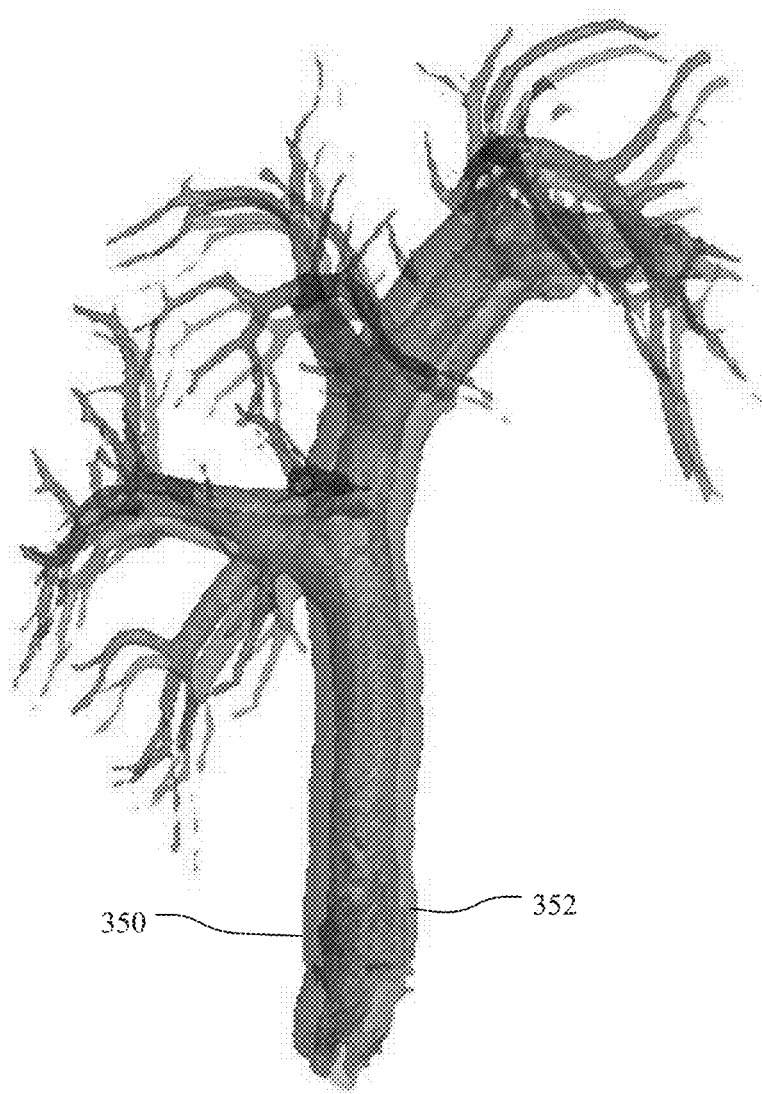
FIG. 16 an image showing simplified movement of the vasculature, for example, limited to only bulk motion caused by respiration.

FIG. 16 shows an illustration for displaying the static roadmap and the dynamic, "moving" vasculature to show the interventional medical device aligned on the static roadmap using the motion transformation. That is, as will be described, alignment of the interventional medical device on the static roadmap can be based on a user selection. The motion adjustment achieves alignment in at least two different display options for the user. For example, motion adjustment can include a motion compensation of the interventional medical device relative to the static roadmap to produce a plurality of images that do not show patient motion. Alternatively, the motion adjustment can be of the static roadmap relative to the interventional medical device to produce a plurality of images that show patient motion.

FIG. 16 shows the vasculature in two different respiratory states. In the illustrated example, the same vasculature is shown in a first position in a first respiratory state 350 and a second position in a second respiratory state 352. As can be seen when overlapping just these two positions of same vasculature during two respiratory states 350, 352, failing to adjust for patient motion obscures information that would, otherwise, be clear. To add further complexity, the above-described systems and methods are not just compensating or adjusting for patient motion during the acquisition of live images 234 of FIG. 3, but must also compensate or adjust the moving, live images 234 relative to the static roadmap 228. Further still, the vasculature is not a rigid structure that simply moves during patient motion. Rather, the vasculature translates, rotates, compresses, extends, and the like. Even beyond all these biological structures, the interventional medical device must be tracked and adjusted relative to the changes in the anatomical structures. Thus, the obscured information caused by vascular movement in live images between two respiratory states, as illustrated in FIG. 16, is only one layer of complexity that the present disclosure addresses.

Figure 17:
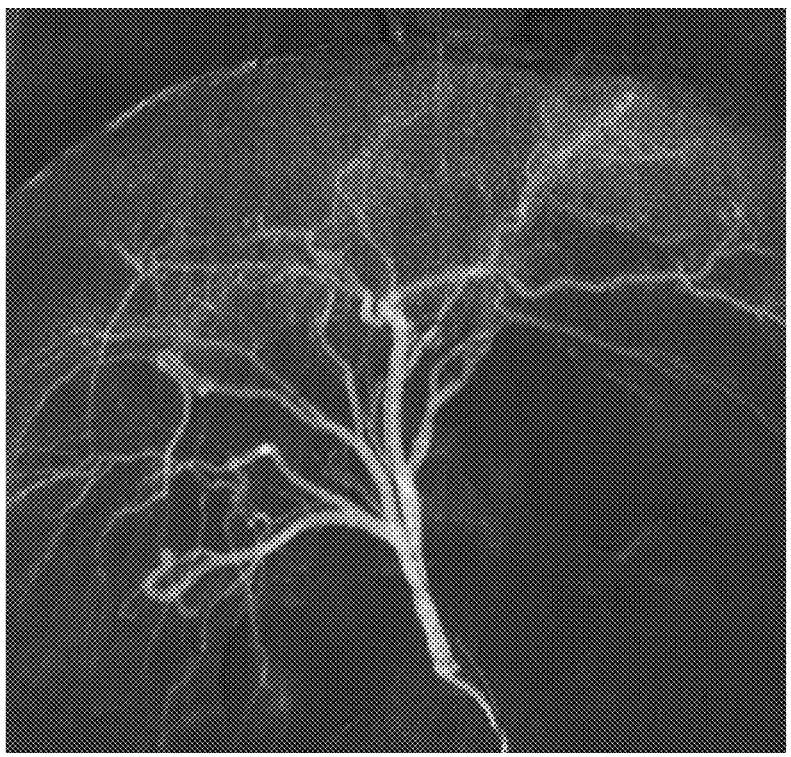
FIG. 17 is a set of two fluoroscopy images generated in accordance with the present disclosure.
Figure 17:
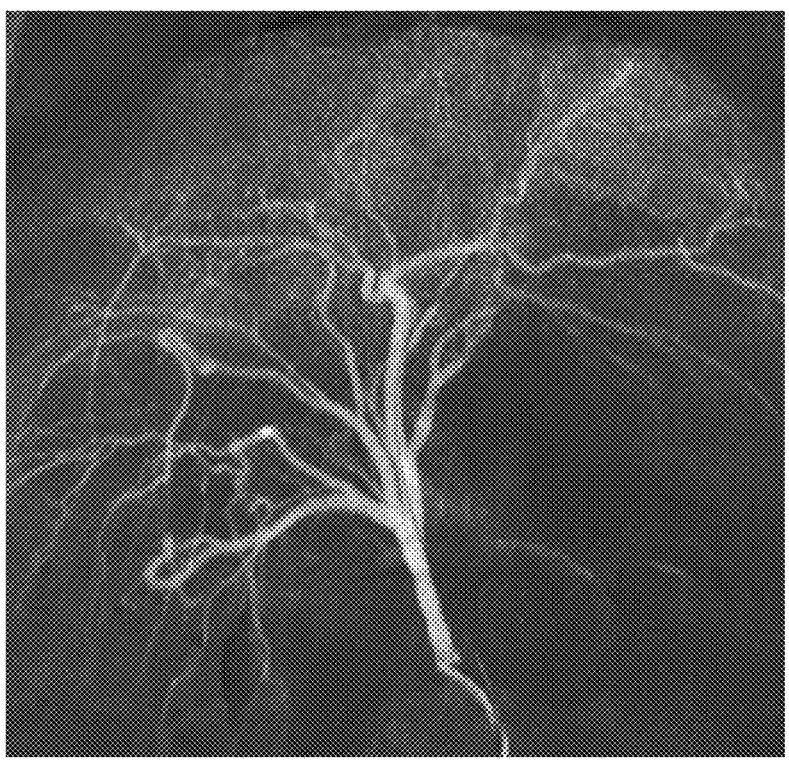

Again, the above-described systems and methods are able to perform motion compensation or motion adjustment across a full range of movement that occurs during time in a patient, including compression, expansion, deformation, translation, rotation, and the like. FIG. 17 shows fluoroscopy images outputted from the first implementation of the guidance system 320 (e.g., with no static vasculature roadmap). The top fluoroscopy image within FIG. 17 shows the vasculature in a more compressed/retracted (e.g., during exhalation), whereas the bottom fluoroscopy image within FIG. 17 shows the vasculature in a decompressed/expanded state (e.g., during inhalation).

Figure 18:
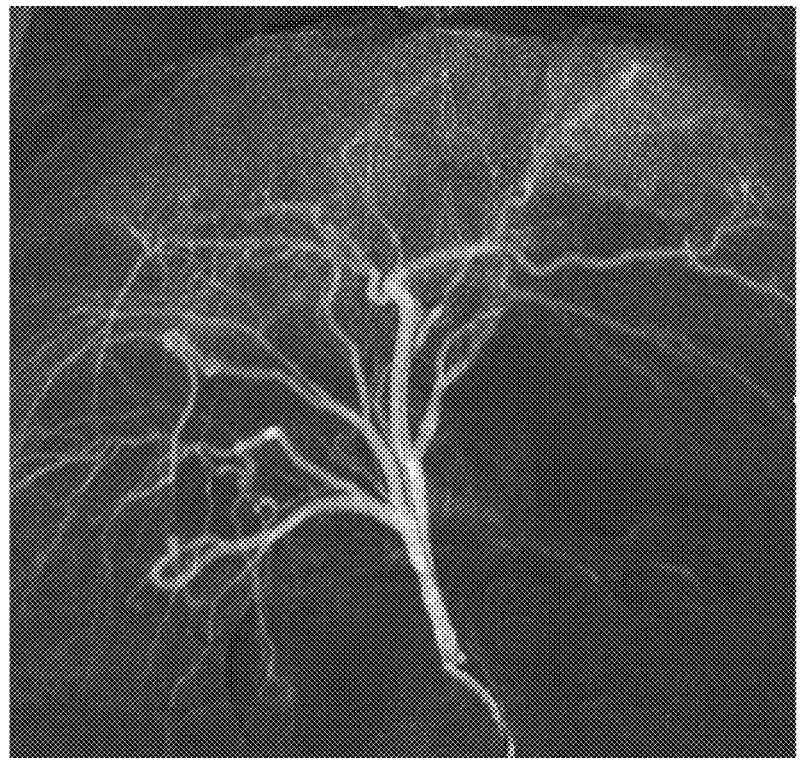
FIG. 18 is a set of two more fluoroscopy images generated in accordance with the present disclosure.
Figure 18:
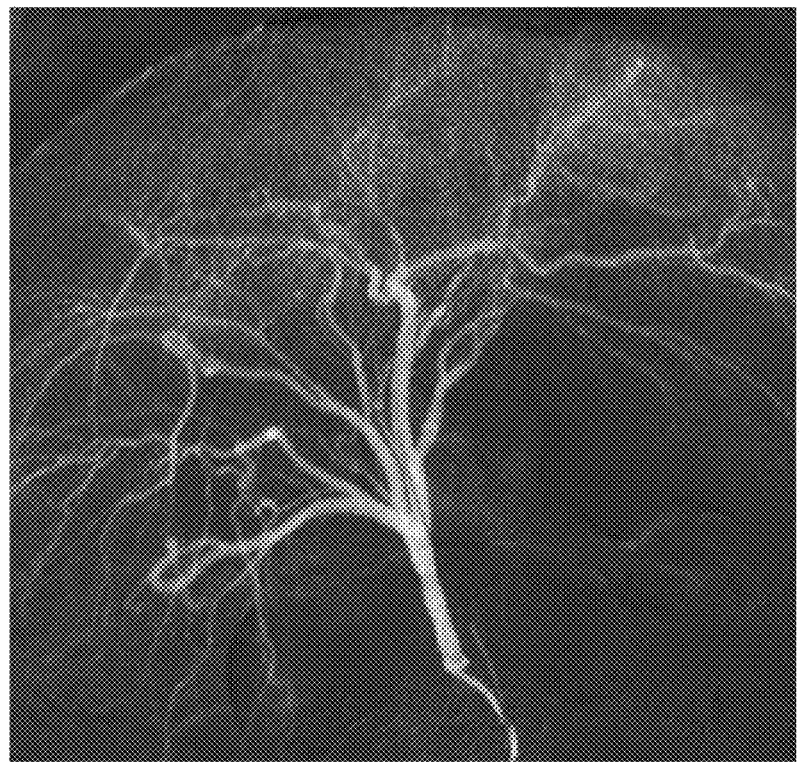

FIG. 18 shows fluoroscopy images outputted from the second implementation of the guidance system 340 (e.g., with the static vasculature image). As shown, the vasculature does not move from the top fluoroscopy image to the bottom fluoroscopy image, which were acquired in different points in time. Rather, each fluoroscopy image shows that only the guidewire moves.

Figure 19:
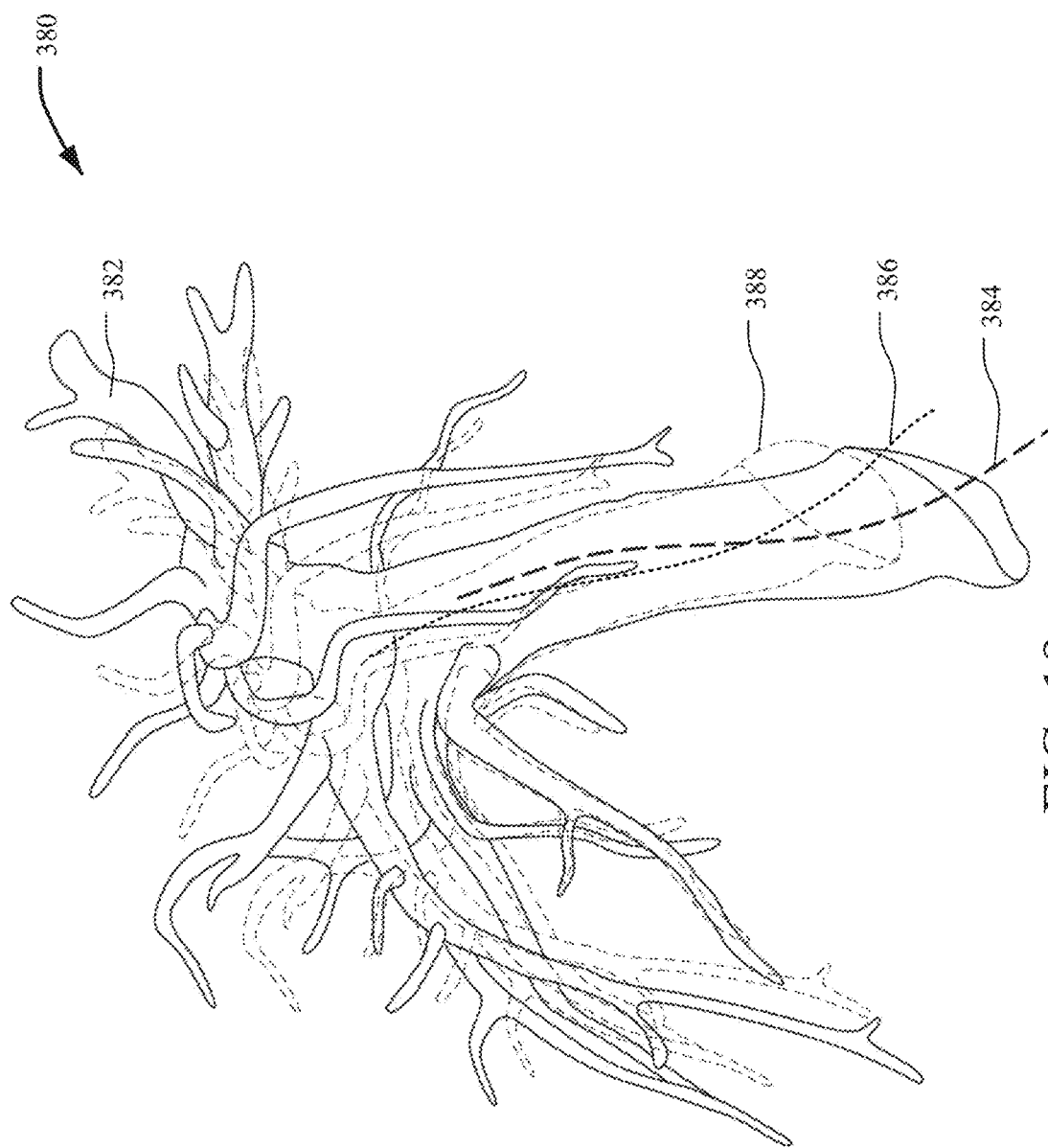
FIG. 19 is an example of a display illustrating user selection between motion compensation and motion adjustment.

As shown in FIG. 19, a display in accordance with the present disclosure is designed to allow a user to select between (1) motion compensation and (2) motion adjustment. That is, a user may use the systems and method described above to display images using motion compensation of the interventional medical device relative to the static roadmap to produce a plurality of images that do not show patient motion. Alternatively, the user may use the system and methods described above to display images using motion adjustment of the static roadmap relative to the interventional medical device to produce a plurality of images that show patient motion.

In particular, referring to FIG. 19, a display 380 in accordance with the present disclosure. The display 380 shows a static vascular roadmap 382 (shown in solid lines). The display 380 also shows an interventional medical device 384. The display 380 is for illustration purposes to show that a user can select between (1) motion compensation of the interventional medical device relative to the static roadmap to produce a plurality of images that do not show patient motion and (2) motion adjustment of the static roadmap relative to the interventional medical device to produce a plurality of images that show patient motion.

If motion compensation is selected, the static vascular roadmap 382 will be shown in a persistent display and the display of interventional medical device 384, which moves in the live images 234 of FIG. 3, is presented as consistently aligned with the static vascular roadmap 382. Thus, this is referred to as "motion compensation" because compensation is applied to remove the appearance of motion for the user. That is, from the fixed external perspective of the user when viewing the display 380 of the images, the static vascular roadmap 382 and interventional medical device 384 do not move with patient motion, such as respiratory motion. Instead, the static vascular roadmap 382 is displayed as a stationary structure and the interventional medical device 384 is aligned therein as it advances through the static vascular roadmap 382.

Alternatively, if motion adjustment is selected, the static vascular roadmap 382 is adjusted to track the motion of the interventional medical device 384 in the live images 234 of FIG. 3. In this way, the static vascular roadmap 382 is motion adjusted between the static position illustrated by the solid lines and tracks with movement of the interventional medical device 384, as it moves to a second position 386. That is, the static vascular roadmap 382 likewise moves to a second position 388 to stay aligned with the interventional medical device 384, as it moves to a second position 386. In this way, patient motion, such as respiratory motion, is shown in the display 380. That is, from the fixed external perspective of the user when viewing the display 380 of the images, the static vascular roadmap 382 and interventional medical device 384 do move with patient motion, such as respiratory motion, such that the static vascular roadmap 382 is displayed as a moving and aligned with the interventional medical device 384 as it advances through the static vascular roadmap 382 and moves to the second position 386.

Although the guidance systems 320, 340 have been described for a two-dimensional implementation of fluoroscopy guidance, in some non-limiting examples, it is desired to have a guidance system that enables three-dimensional guidance. A three-dimensional guidance system 400 utilizes some previously disclosed components. Thus, components already discussed above, also pertain to the three-dimensional guidance system 400.

Figure 20:
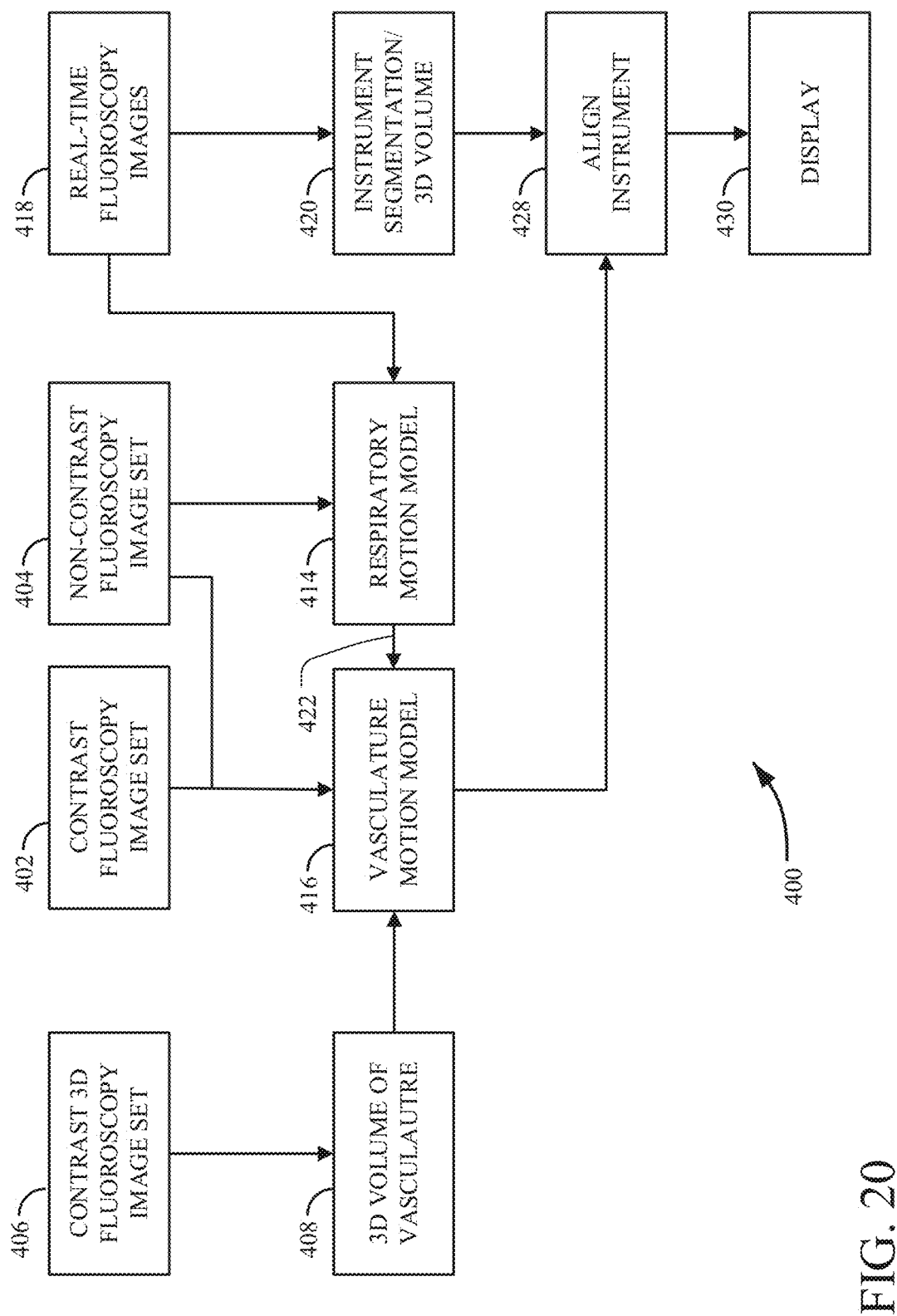
FIG. 20 a block diagram illustrating one, non-limiting example for implementing a three-dimensional ("3D") fluoroscopy guidance system in accordance with the present disclosure.

FIG. 20 is a block diagram of the three-dimensional guidance system 400, which can be implemented on the x-ray imaging system 100 (or modified variants discussed above) and can include the acquisition of a contrast 2D fluoroscopy image set 402, a non-contrast 2D fluoroscopy image set 404, and a 3D contrast x-ray image set 406. The contrast 2D fluoroscopy image set 402 and the non-contrast 2D fluoroscopy image set 404 can be identical to the image sets 324, 322, respectively (e.g., both image sets contain fluoroscopy images throughout the entire respiratory cycle). Alternatively, the images sets 402, 404 can be acquired by using the procedure below.

In some non-limiting examples, the desired fluoroscopy imaging vasculature can be the portal venous system, and can be acquired by performing a superior mesenteric arteriogram. In order to inject the contrast agent, an angiographic catheter (e.g., sized 5Fr) can be placed in the superior mesenteric artery under fluoroscopic image guidance, and the contrast agent (e.g., iodine) can be injected followed by a saline injection. As the injected contrast agent is draining from the superior mesenteric artery to the portal veins, fluoroscopy images are acquired (e.g., via the single mode, or biplane mode of the imaging system 100). For example, the contrast 2D fluoroscopy image set 402 can be obtained at a specific sampling rate (e.g., 15 frames per second), and includes fluoroscopy images throughout the patient's entire respiratory cycle. After the contrast agent has drained (e.g., no remnant of the contrast agent remains in the vasculature), or conversely, prior to injecting the contrast agent, the non-contrast 2D fluoroscopy image set 404 can be acquired, such that the image set includes fluoroscopy images throughout the patient's entire respiratory cycle.

Once the image sets 402, 404 are acquired, or prior to the acquisition of both, the 3D contrast x-ray image set 406 can be acquired. The 3D image set can be acquired by first using an intra-arterial injection (e.g., in the superior mesenteric artery), followed by a saline injection. Subsequent to the injection, a breath hold is performed by the patient during acquisition of the image set 406. Specifically, the image set 406 includes x-ray images that are acquired at two different spatial positions of the x-ray detector array assembly 106. For example, multiple x-ray images, within the 3D contrast x-ray image set 406, are acquired at different pivoting angles of the x-ray source assembly 104 and the x-ray detector array assembly 106 about the horizontal pivoting axis 116. Thus, images within the image set 406 are acquired at multiple planes. In some non-limiting examples, the pivoting angles can be from 0° to 360°, with any step size in between. In other non-limiting examples, only two fluoroscopy images within the image set 406 need to be from separate planes to extrapolate the 3D volume of the vasculature. In still further non-limiting examples, to avoid the additional radiation and contrast injection from the acquisition of both contrast image sets 402, 406, the 3D contrast fluoroscopy image set 406 can be obtained during the acquisition of the contrast 2D fluoroscopy image set 402. For example, a specific target location can be chosen and if fluoroscopy images from two different planes are acquired, the 3D location can be determined by the intersection of the back-projection of the 2D points in the 3D volume space, which will be discussed in more detail below.

Once the 3D contrast x-ray image set 406 is acquired, a 3D volume can be generated. Then, the 3D volume of the vasculature 408 (e.g., the portal venous system) can be extracted, or removed from the 3D volume (e.g., from other anatomical portions in the 3D volume). This can be accomplished, for example, by first applying a Gaussian filter (e.g., standard deviation of 1.5) to reduce noise. Then, a global thresholding approach can also be used (e.g., threshold=−250), to extract just the 3D volume of the vasculature 408, similar to the procedure used to generate the vasculature motion model 230. Additionally, a connected component analysis can be performed to find all connected regions in the binarized volume. In some cases, only the largest region can be used to represent the vasculature. For example, smaller regions can be manually parsed out and deleted, as they are typically noise and artifacts. The output from these yields the 3D volume of the vasculature 408.

Although the respiratory motion tracking utilizes a different process to track the respiratory state, the extraction of the curvilinear features could be substituted to determine the respiratory state (e.g., substituted for the respiratory motion calculation 414). The guidance system 400 includes generating a respiratory motion model 414, which utilizes the difference in brightness between regions within fluoroscopy images, where the regions can include locations above and below the diaphragm. Specifically, to generate the respiratory motion model 414, the mean brightness in the x-dimension can be calculated for a given fluoroscopic image within the image set 404. For example, calculating the mean brightness in the x-dimension can help to reduce information, which is represented by $\Sigma_{x=1}^{n_x} I_t(x,y)$ in equation 11. Essentially, the output from using either the mean or the sum in the x-dimension, is identical because the mean-normalization cancels out in equation 11. In some non-limiting examples, alternatively to calculating the mean brightness in the x-dimension, the sum, maximum, median, minimum, etc., could also be used to reduce information. The x-dimension calculation can be used to determine the center of mass in the y-dimension, which is used as an indicator of the respiratory state. Specifically, the center of mass in the y-dimension relates to the point (in the y-direction), where the sum of all pixel values above the center of mass is the same as the sum of all pixel values below the center of mass. The center of mass in the y-direction is calculated the same as r(t) is calculated. Once the center of mass in the y-dimension is calculated for a given image, the respiratory state r(t) is related to the center of mass in the y-direction according to equation 11. This procedure is used to calculate the respiratory state for all the given images within the non-contrast 2D fluoroscopy image set 404. With regard to equation 11, the variable t denotes the time and $I_t(x,y)$ is the fluoroscopic image acquired at time t. This approach can be used for either single or biplane acquisitions. For biplane data, the respiratory state calculated for each image is averaged.

$$r(t) = \frac{\sum_{y=1}^{n_y} y \frac{1}{n_x} \sum_{x=1}^{n_x} I_t(x, y)}{\sum_{y=1}^{n_y} \frac{1}{n_x} \sum_{x=1}^{n_x} I_t(x, y)} \quad (11)$$

Figure 21:
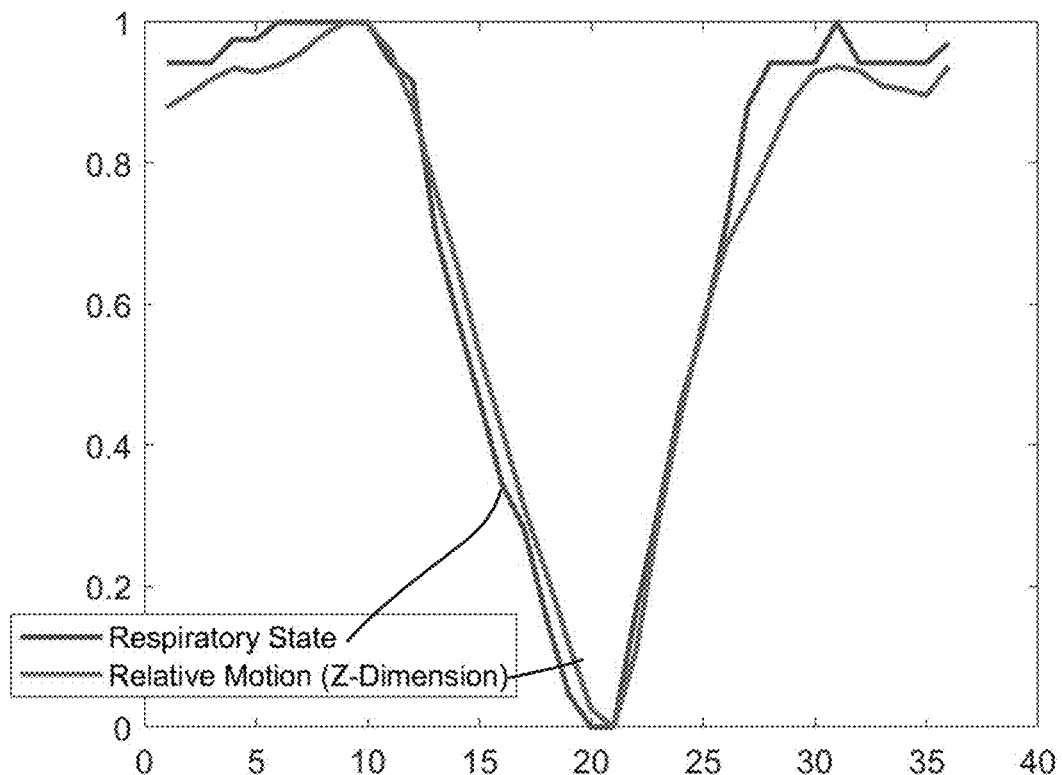
FIG. 21 is a graph of the respiratory state vs. the relative motion of the vasculature in the Z-dimension in accordance with the present disclosure.

FIG. 21 shows a graph of the output of equation 11 (e.g., the respiratory state), vs. the estimated motion of the vasculature in the Z-dimension. As shown, the respiratory state corresponds closely to the relative motion of the vasculature in the Z-dimension.

Referring again to FIG. 20, to create the vasculature motion model 416, the contrast image set 402 and the non-contrast image set 404 are subtracted. More specifically, for each frame within the contrast image set 402, there are far more corresponding frames within the native 2D image set 404. Thus, for each frame within the contrast image set 402 at an acquisition time, five of the best corresponding frames within the non-contrast image set 404 that correspond with that acquisition time are chosen. For example, to identify image pairs the mean squared error can be calculated and minimized to generate pairs of contrast and non-contrast frames. This is similar to the procedure regarding equation 1. However, typically, as discussed above, there are more non-contrast images than contrast images. Thus, for each contrast image there are a number of matched non-contrast images (e.g., 5, 10, etc.). The best matches from the number of matched non-contrast images can be selected, for example 5 best matches, or alternatively the single best match can be used. If more than one best match is used, the images are averaged. Then, the corresponding contrast image is subtracted from the average image based on the best matches from the non-contrast images, or subtracted from the best matched non-contrast image. This subtraction is completed for all contrast images. The subtraction removes any anatomical background.

Then, to create the vasculature motion model 416, a cost function CF is defined, which projects all points from the 3D volume of the vasculature 408 into the 2D image space. Once the 3D volume 408 is projected into the 2D image space, the average squared brightness is calculated for all projected points in the subtracted image, where the output is defined as the cost.

Then, the cost function above is used to evaluate all subtracted image frames. Once evaluated, the subtracted 2D frame with the lowest cost is identified and chosen as start frame. This subtracted 2D frame is used to perform a 3D to 2D registration by minimizing the cost function to estimate an affine transformation matrix. The minimization is performed using a regular step gradient descent algorithm. The algorithm is applied to blurred versions of the subtracted image with different blurring kernels, starting with a large kernel to allow larger translations. In the first steps only rigid motion is taken into account and later affine parameters are included. A regularization term can be added to the cost function to avoid large deformations of the vasculature. After, the 3D to 2D registration is applied to the remaining subtracted image frames. In some non-limiting examples, the result of the previous frame, or next frame is used as initialization.

After generating a transformation matrix for each subtracted 2D frame, a linear function, or in some cases a parametrization discussed above, is estimated for each parameter of the transformation matrix, which maps or relates the respiratory state to the respective parameter. Thus, the respiratory state for each subtracted 2D frame is used as x, and the parameter of each subtracted 2D frame is used as y. A robust regression approach using a bisquare cost function is then used to estimate, and generate a linear relationship between the respiratory state and the parameter within the transformation matrix.

In some non-limiting examples, as discussed above, the 3D volume of the vasculature 408 is generated only via two different planes of fluoroscopy images. Thus, in some cases, the contrast fluoroscopy image set 402 can be used to generate the 3D volume of the vasculature 408, and the generation of the vasculature motion model 416 will be slightly different. For example, this alternative approach does not use the acquired 3D DSA, rather a target is defined in both frames of the 2D projection images. This target position is tracked over time using the surrounding neighborhood of the target position. For all subsequent frames, a cost function is minimized, which calculates the mean squared error between the patch around the target in the original image and around the transformed target in the current image. After tracking the target in both image sequences, the respective 3D positions can be calculated for each 2D subtracted frame by determining the projection ray into the 3D volume for both planes and calculating the intersection (or the closest point to both lines if there is not exact intersection) to generate the 3D volume 408. Then, a linear relationship between the 3D target position and the respiratory state is estimated using a 3-element translation vector to create the vasculature motion model 416, rather than using the affine transformation matrix discussed above.

Once the respiratory motion model 414 and the vasculature motion model 416 have been generated, a 3D volume of the instrument at 420 can be generated. First, real-time fluoroscopy images 418 are acquired via the x-ray imaging system 100, which include the instrument acquired from different planes. Then, these images within the real-time fluoroscopy images 418 are processed to segment the instrument, and create a 3D volume of the instrument (e.g., at 420). In order to segment the instrument, the mean squared error of the current image relative to every non-contrast image frame is calculated and the best non-contrast image frame (e.g., the one having the lowest error) is subtracted from the given/current image. A line detection filter is then applied, and subsequently a dynamic threshold is applied, which changes with the average intensity of each image row to binarize the image. In some non-limiting examples, rather than this process, the instrument segmentation can be performed by using a neural network (e.g., the neural network 300 as previously described).

After the segmented 2D images are binarized, the segmented binarized 2D images are thinned using topology preserving thinning and all possible curvilinear segments are extracted. Then, a 2D path search is applied, which finds a single connected path that represents the centerline of the instrument. The set of curvilinear segments represents a directed graph, where each segment represents a node and the connection weights are defined by the Euclidean distance between the endpoints of the two segments and the angle between the segments. Additionally, the number of points of all unused segments are added to the final cost of each path. Dijkstra's approach is used to find the path which minimizes the overall costs through the segments. After the 2D device path was segmented (or outputted from the neural network 300) for two real time images that were acquired from two different planes, pairs of corresponding points from the two planes are identified, which represent the same 3D point. This can be done by constructing a 2D image, where each pixel represents a potential point pair, all pixels from left to right represent the points on the device path from the first plane (starting at the tip), and the pixels from top to bottom represent points on the second plane (starting at the tip). The value of each pixel is the distance between the projection 3D rays from the focal point to the respective point on the 2D plane. The monotonic function then identifies the point correspondences that can be determined by finding the path that minimizes the costs through the image starting from the top, left pixel to either the bottom or right border. Every pixel on the path represents one point correspondence. The 3D device path is then calculated by reconstructing each pair of corresponding points separately, where the points are back-projected into the volume space and the intersection (or the closest point to both lines) represents the 3D position. This procedure generates a 3D centerline of the instrument at step 420. Then, if the 3D centerline is determined, a 3D volume of the instrument can also be generated at step 420. For example, the cross-section of the instrument (or any desired cross-section) and diameter of the instrument (or any desired diameter) is used to extrude along the 3D centerline to generate a 3D volume of the instrument. Alternatively, the 3D centerline approach may only be used for initialization. For example, for all subsequent frames (e.g., within the real-time fluoroscopy images 418), the instrument can be tracked using 3D to 2D registration. This allows reconstruction without segmenting the device first and may be more robust in some cases. Thus, a point cloud representing the 3D device centerline from the previous frame is forward projected into the 2D image space and a cost function based on the average squared brightness is calculated. Then, an affine transform is estimated by minimizing the cost function (e.g. using Nelder-Mead Simplex approach) to determine changes in the instrument position and orientation compared to the previous time frame. If P represents the set of points representing the device centerline from the previous frame, the transform can be determined based on the current live image I by equation 12.

$$T_f = \underset{T}{\mathrm{argmax}} \sum_{\forall x \in P} I(T \cdot x)^2 \quad (12)$$

The new device position can then be described by equation 13 the set of points being $P_n$.

$$P_n = \{T \cdot x_0, T \cdot x_1, \ldots T \cdot x_n\}. \quad (13)$$

Once the respiratory motion model 414, the vasculature motion model 416, and the 3D volume of the instrument are generated, the interventional radiology procedure can proceed. As discussed above, the real-time fluoroscopy images 418 can be directed to the respiratory motion model 414 to determine the respiratory state r(t), indicated by reference numeral 422. After the respiratory state r(t) 422 has been determined, the respiratory state is inputted into the vasculature motion model 416 to generate the corresponding transformation matrix (or the 3-element translation vector), from the previously calculated linear relationship (e.g., the estimated linear relationship between the transformation matrix/3-element translation vector and the respiratory state).

The align instrument step 428 can be implemented on the operator workstation 122, the networked workstation 148, and the like, and can apply motion compensation to either the 3D volume of the instrument or the 3D volume of the vasculature 408. In a first implementation, the align instrument step 428 receives the transformation matrix/3-element translation vector, which corresponds to the respiratory state 422, inverses the transformation matrix/3-element translation vector and applies this to the 3D volume of the instrument, spatially manipulating the instrument. Alternatively, however, in some non-limiting examples, the inverses of the transformation matrix/3-element translation vector can be applied to the 3D centerline of the instrument and, subsequently, the spatially manipulated 3D centerline can be extruded to generate a 3D volume of the instrument that is spatially manipulated. Then, the 3D volume of the vasculature 408 can be superimposed with the motion compensated 3D volume of the instrument and can be displayed on the display 430 (e.g., similar to the display 150, the display 124, etc.). This allows for a relatively static representation of the vasculature (e.g., the 3D volume of the vasculature) to be aligned with the motion compensated 3D volume of the instrument, such that apparent motion of the instrument can be only caused by the manipulation by the interventional radiologist.

The align instrument step 428 can also apply motion compensation to the 3D volume of the vasculature 408. For example, the align instrument step 428 receives the transformation matrix/3-element translation vector (e.g., from the vasculature motion model 416), which corresponds to the respiratory state 422 and applies this to the 3D volume of the vasculature 408. Then, this spatially manipulated 3D volume of the vasculature can be superimposed with the 3D volume of the instrument at step 420 to display it on the display 430. This allows for the medical instrument to be aligned on a spatially moving 3D representation of the vasculature. In some non-limiting examples, the interventional radiologist can easily switch/toggle between either implementation scheme (e.g., the align instrument step 428).

The movement data (e.g., a translation matrix/3-element translation vector above) that relates to the spatial manipulation of the different portions of the vasculature from one respiratory state to another, can be used to generate a 3D motion compensated representation of the vasculature, or alternatively, a 3D motion compensated representation of the medical instrument. For example, if the respiratory state is known, then the movement data indicating how the vasculature should move is also known for that respiratory state. This movement data can then be applied to a 3D volume of the vasculature (e.g., at r(t) for a fully inhaled or exhaled state) to manipulate the 3D volume of the vasculature within the viewing plane, such that the 3D volume represents the realistic orientation of the vasculature at that respiratory state. Alternatively, this movement data can also be applied to the medical instrument to move the medical instrument based on the movement of particular locations of the 3D volume of the vasculature. For example, if a medical instrument 460 resides in a portion of the vasculature that translates, rotates, compresses, extends, etc., then the inverse of this movement of the vasculature will be applied to the medical instrument. This can be advantageous for example, as the target (e.g., the vasculature) can be a static 3D volume, while the instrument can be moved (e.g., compressed, extended, rotated, translated), based on the movement of the vasculature for that particular respiratory state. As noted above, the interventional radiologist can toggle between a first state of the guidance system 400, where the movement data is applied to the 3D volume of the vasculature to move the 3D volume of the vasculature within the viewing plane (e.g., to compensate for respiratory motion of the vasculature), and a second state of the guidance system 400, where the movement data is applied to a 3D volume of the medical instrument to move the 3D volume of the medical instrument within the viewing plane (e.g., to compensate for respiratory motion of the vasculature), based on a user selection.

The above-described system may be configured or otherwise used to carry out processes in accordance with the present disclosure. In particular, as will be described in further detail, The present invention has been described in terms of one or more preferred non-limiting examples, and it should be appreciated that many equivalents, alternatives, variations, and modifications, aside from those expressly stated, are possible and within the scope of the invention.

The invention claimed is:

1. A method of creating motion-adjusted images of a patient to guide an interventional medical procedure, the method comprising:
    acquiring a first plurality of images of a patient having non-contrast enhanced vasculature;
    acquiring a second plurality of images of the patient having contrast enhanced vasculature;
    generating a static roadmap of vasculature of the patient using the first plurality of images and the second plurality of images;
    generating a motion model of the patient using the first plurality of images and the second plurality of images;
    acquiring a third plurality of images of the patient with an interventional medical device deployed within the patient, the third plurality of images being different than the first plurality of images;
    generating motion tracking data of one of the patient or the interventional medical device using the third plurality of images;
    generating a motion transformation using the motion tracking data and the motion model;
    displaying the static roadmap and the third plurality of images to show the interventional medical device aligned on the static roadmap using the motion transformation, and
    wherein alignment of the interventional medical device on the static roadmap is based on a user selection of one of:
        motion compensation of the interventional medical device relative to the static roadmap to produce a plurality of images that do not show patient motion; and
        motion adjustment of the static roadmap relative to the interventional medical device to produce a plurality of images that show patient motion.

2. The method of claim 1 further comprising extracting the interventional medical device from the third plurality of images using a neural network to generate, for each image of the third plurality of images, a continuous and connected image of the medical device.

3. The method of claim 1 further comprising generating the motion model by determining curvilinear features using the first plurality of images.

4. The method of claim 1 further comprising determining the motion model by determining curvilinear features within third plurality of images.

5. The method of claim 1 further comprising determining a respiratory state of the patient using the third plurality of images and using the motion model and the respiratory state to determine motion adjustments reflected in the motion transformation.

6. The method of claim 5 wherein determining the respiratory state of the patient includes calculating a mean brightness in one dimension using the third plurality of images.

7. The method of claim 6 wherein the respiratory state of the patient is determined using a transformation configured to generate a translation vector for one or more pixels within the third plurality of images.

8. The method of claim 1 wherein at least one of the first plurality of images, the second plurality of images, and the third plurality of images includes three-dimensional images.

9. The method of claim 1 wherein motion compensation of the interventional medical device relative to the static roadmap to produce a plurality of images that do not show patient motion presents a static display relative to the user illustrating only movement of the interventional medical device due to advancement by the user.

10. The method of claim 1 wherein motion adjustment of the static roadmap relative to the interventional medical device to produce a plurality of images that show patient motion presents a dynamic display relative to the user illustrating movement of patient and the interventional medical device due to physiological motion and advancement of the interventional medical device by the user.

11. The method of claim 1, wherein alignment of the interventional medical device on the static roadmap in a first display shows motion compensation of the interventional medical device relative to the static roadmap to produce a plurality of images that do not show patient motion,
    alignment of the interventional medical device on the static roadmap in a second display shows motion adjustment of the static roadmap relative to the interventional medical device to produce a plurality of images that show patient motion, and
    a user selection can switch between the first display and the second display.

12. A fluoroscopy imaging system comprising:
    an x-ray source assembly coupled at one end and a x-ray detector array assembly coupled at an opposing end;
    a computer system configured to:
        control the x-ray source assembly and the x-ray detector array assembly to acquire a first plurality of images of a patient having non-contrast enhanced vasculature;
        control the x-ray source assembly and the x-ray detector array assembly to acquire a second plurality of images of the patient having contrast enhanced vasculature;
        generate a static roadmap of vasculature of the patient using the first plurality of images and the second plurality of images;
        generate a motion model of the patient using the first plurality of images and the second plurality of images;
        control the x-ray source assembly and the x-ray detector array assembly to acquire a third plurality of images of the patient with an interventional medical device deployed within the patient, the third plurality of images being different than the first plurality of images;

generate motion tracking data of one of the patient or the interventional medical device using the third plurality of images;

generate a motion transformation using the motion tracking data and the motion model;

display the static roadmap and the third plurality of images to show the interventional medical device aligned on the static roadmap using the motion transformation and, wherein alignment of the interventional medical device on the static roadmap is based on a user selection of one of:

motion compensation of the interventional medical device relative to the static roadmap to produce a plurality of images that do not show patient motion; and motion adjustment of the static roadmap relative to the interventional medical device to produce a plurality of images that show patient motion.

13. The system of claim 12 wherein the computer system is further configured to extract the interventional medical device from the third plurality of images using a neural network.

14. The system of claim 12 wherein the computer system is further configured to generate the motion model by determining curvilinear features using the first plurality of images.

15. The system of claim 12 wherein the computer system is further configured to generate the motion transformation by determining curvilinear features within third plurality of images.

16. The system of claim 12 wherein the computer system is further configured to determine a respiratory state of the patient using the third plurality of images and use the motion model and the respiratory state to determine motion adjustments reflected in the motion transformation.

17. The system of claim 16 wherein the computer system is further configured to calculate a mean brightness in one dimension using the third plurality of images to determine the respiratory state of the patient includes.

18. The system of claim 17 wherein the computer system is further configured to use a transformation configured to generate a translation vector for one or more pixels within the third plurality of images to determine the respiratory state of the patient.

19. The system of claim 12 wherein at least one of the first plurality of images, the second plurality of images, and the third plurality of images includes three-dimensional images.

20. The system of claim 12 wherein motion compensation of the interventional medical device relative to the static roadmap to produce a plurality of images that do not show patient motion presents a static display relative to the user illustrating only movement of the interventional medical device due to advancement by the user.

21. The system of claim 12 wherein motion adjustment of the static roadmap relative to the interventional medical device to produce a plurality of images that show patient motion presents a dynamic display relative to the user illustrating movement of the patient and the interventional medical device due to physiological motion and advancement of the interventional medical device by the user.

22. The system of claim 12, wherein alignment of the interventional medical device on the static roadmap in a first display shows motion compensation of the interventional medical device relative to the static roadmap to produce a plurality of images that do not show patient motion, alignment of the interventional medical device on the static roadmap in a second display shows motion adjustment of the static roadmap relative to the interventional medical device to produce a plurality of images that show patient motion, and a user selection can switch between the first display and the second display.

23. A method of creating motion-adjusted images of a patient to guide an interventional medical procedure, the method comprising:

acquiring a plurality of images of the patient having contrast enhanced vasculature;

generating a static roadmap of vasculature of the patient using the plurality of images;

generating a motion model of the patient using the plurality of images;

acquiring another plurality of images of the patient with an interventional medical device deployed within the patient;

generating motion tracking data of one of the patient or the interventional medical device using the another plurality of images;

generating a motion transformation using the motion tracking data and the motion model;

displaying the static roadmap and the another plurality of images to show the interventional medical device aligned on the static roadmap using the motion transformation, alignment of the interventional medical device on the static roadmap in a first display shows motion compensation of the interventional medical device relative to the static roadmap to produce a plurality of images that do not show patient motion, alignment of the interventional medical device on the static roadmap in a second display shows motion adjustment of the static roadmap relative to the interventional medical device to produce a plurality of images that show patient motion, and a user selection can switch between the first display and the second display.

* * * * *